(12) United States Patent
Namsaraev et al.

(10) Patent No.: US 11,603,553 B2
(45) Date of Patent: Mar. 14, 2023

(54) METHODS OF ANALYZING NUCLEIC ACID FRAGMENTS

(71) Applicant: Grail, LLC, Menlo Park, CA (US)

(72) Inventors: Eugeni Namsaraev, Palo Alto, CA (US); Maneesh Jain, San Francisco, CA (US)

(73) Assignee: GRAIL, LLC, Menlo Park, CA (US)

( * ) Notice: Subject to any disclaimer, the term of this patent is extended or adjusted under 35 U.S.C. 154(b) by 0 days.

(21) Appl. No.: 16/824,417

(22) Filed: Mar. 19, 2020

(65) Prior Publication Data

US 2020/0248234 A1 Aug. 6, 2020

Related U.S. Application Data

(63) Continuation of application No. 15/673,883, filed on Aug. 10, 2017, now Pat. No. 10,626,443.

(60) Provisional application No. 62/373,332, filed on Aug. 10, 2016.

(51) Int. Cl.
  *C12Q 1/6806* (2018.01)
  *C12Q 1/6816* (2018.01)
  *C12Q 1/6827* (2018.01)
  *C12Q 1/6874* (2018.01)
  *C12N 15/10* (2006.01)
  *C12N 15/11* (2006.01)
  *C12Q 1/6837* (2018.01)
  *C12Q 1/6855* (2018.01)

(52) U.S. Cl.
  CPC ......... *C12Q 1/6806* (2013.01); *C12Q 1/6816* (2013.01); *C12Q 1/6827* (2013.01); *C12Q 1/6874* (2013.01); *C12N 15/10* (2013.01); *C12N 15/11* (2013.01); *C12N 2310/531* (2013.01); *C12Q 1/6837* (2013.01); *C12Q 1/6855* (2013.01)

(58) Field of Classification Search
  CPC ............ C12Q 1/6806; C12Q 2535/122; C12Q 2537/159; C12Q 2529/119; C12Q 1/6874; C12Q 2525/307; C12Q 2521/313; C12Q 1/6827; C12Q 1/6816; C12N 15/10; C12N 15/11; C12N 2310/531
  See application file for complete search history.

(56) References Cited

U.S. PATENT DOCUMENTS

| | | | |
|---|---|---|---|
| 10,767,222 B2 | 9/2020 | Lin et al. | |
| 2005/0095645 A1 | 5/2005 | Jones et al. | |
| 2007/0231823 A1 | 10/2007 | Mckernan et al. | |
| 2012/0208711 A1* | 8/2012 | Cortese | C12Q 1/6837 506/2 |
| 2012/0316074 A1* | 12/2012 | Saxonov | C12N 15/1075 506/2 |
| 2013/0090250 A1 | 4/2013 | Sparks et al. | |
| 2013/0310263 A1 | 11/2013 | Lo et al. | |
| 2016/0201142 A1 | 7/2016 | Lo et al. | |
| 2016/0304954 A1 | 10/2016 | Lin et al. | |
| 2018/0066306 A1 | 3/2018 | Namsaraev | |
| 2018/0251848 A1* | 9/2018 | Diehn | C12Q 1/6886 |

FOREIGN PATENT DOCUMENTS

| | | |
|---|---|---|
| WO | WO-2015100427 A1 | 7/2015 |
| WO | WO-2016040901 A1 | 3/2016 |
| WO | WO-2018031808 A1 | 2/2018 |

OTHER PUBLICATIONS

Boddy, et al., "The role of cell-free DNA size distribution in the management of prostate cancer", Oncology Research, vol. 16, No. 1, 2006, 35-41.
Mouliere et al. High fragmentation characterizes tumour-derived circulating DNA. PLoS ONE 6(9):e23418 (2011).
Zill, et al., "Cell-Free DNA Next-Generation Sequencing in Pancreatobiliary Carcinomas", Cancer Discovery vol. 5, No. 10, 2015, 1040-1048.
Agilent Technologies Inc., Protocol version 1.2, pp. 1-54, April (Year:2009).
Bettegowda et al. Detection of Circulating Tumor DNA in Early- and Late-Stage Human Malignancies. Sci. Transl. Med. 6(224):224ra24 (2014).
Chan, KCA, et. al. Early detection of nasopharyngeal carcinoma by plasma epstein-barr virus DNA analysis in a surveillance program. Cancer 2013;119:1838-44.
Gerlinger et al. Intratumor heterogeneity and branched evolution revealed by multiregion sequencing. N Engl J Med 366(10):883-892 (2012).
International Application No. PCT/US2017/046351 International Search Report and Written Opinion dated Nov. 20, 2017.
Lawrence, et al. Mutational heterogeneity in cancer and the search for new cancer genes. Nature 2013; 499: 214-218.
NimbleGen System Inc., Technical Notes, http://www.nimblegen.com, pp. 1-4, February (Year: 2008).
U.S. Appl. No. 15/673,883 Notice of Allowance dated Dec. 13, 2019.
U.S. Appl. No. 15/673,883 Office Action dated Apr. 29, 2019.

* cited by examiner

*Primary Examiner* — Cynthia B Wilder

(57) ABSTRACT

Provided herein are methods for enriching a biological sample for a target nucleic acid, and analyzing the nucleic acid. In some cases, a biological sample is enriched for target nucleic acids associated with a cancer or tumor. In some cases, a biological sample is enriched for target nucleic acids, and the target nucleic acids vary in length. In some cases, one or more probes are used to enrich the biological sample for the target nucleic acid. In some cases, one or more probes hybridize to one or more ends of a target nucleic acid.

17 Claims, 26 Drawing Sheets

Specification includes a Sequence Listing.

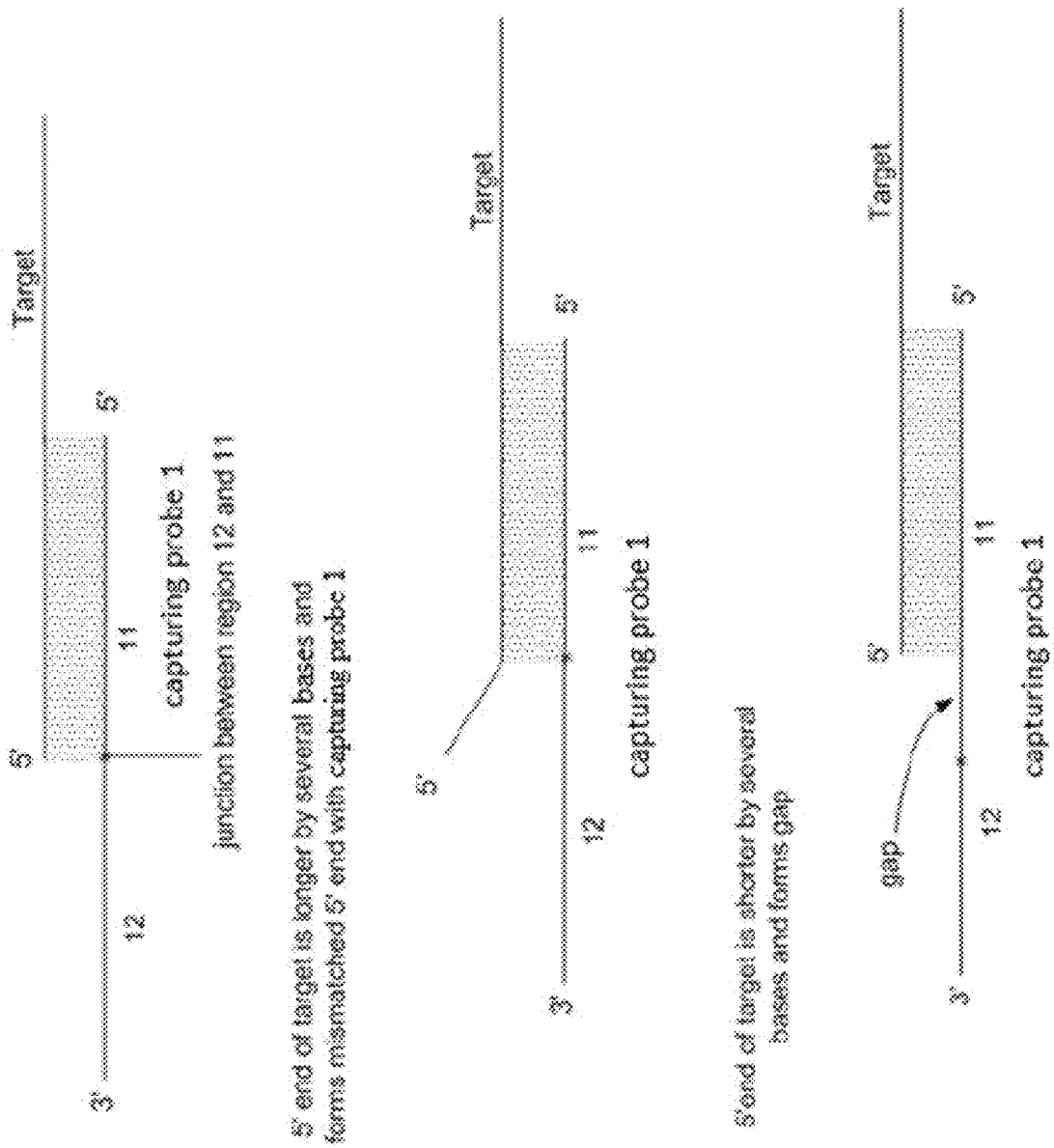

Fig. 1C
perfectly matched 3' end position between target and capturing probe 2
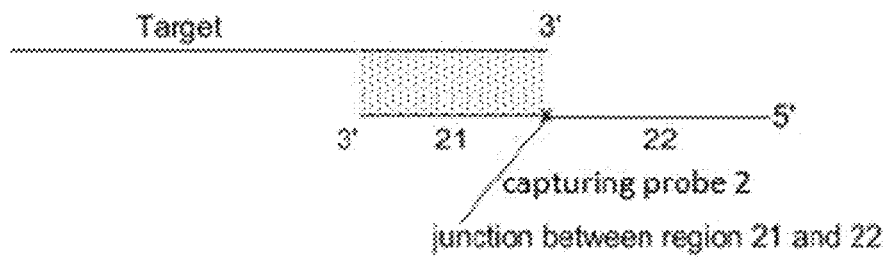
3' end of the target is longer by several bases and form mismatched 3' end with capturing probe 2
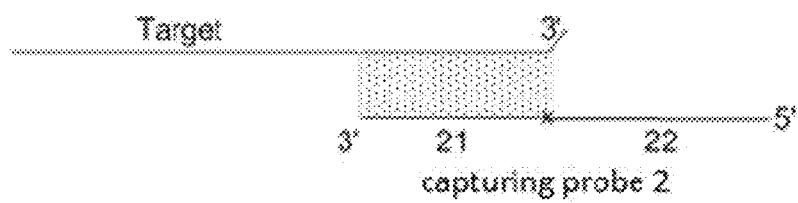
3' end of the target is shorter by several bases and form gap at unpaired bases
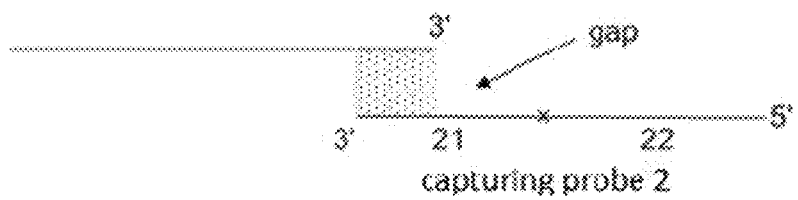

Fig. 3B
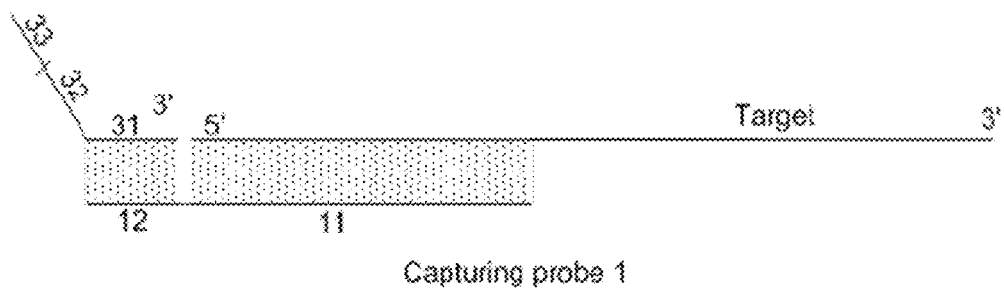
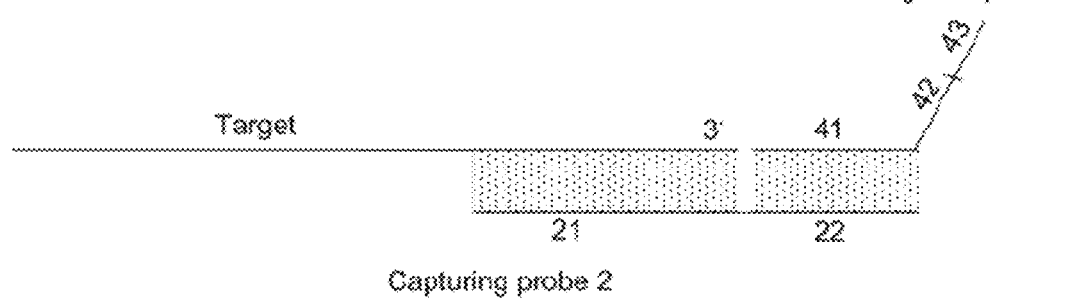

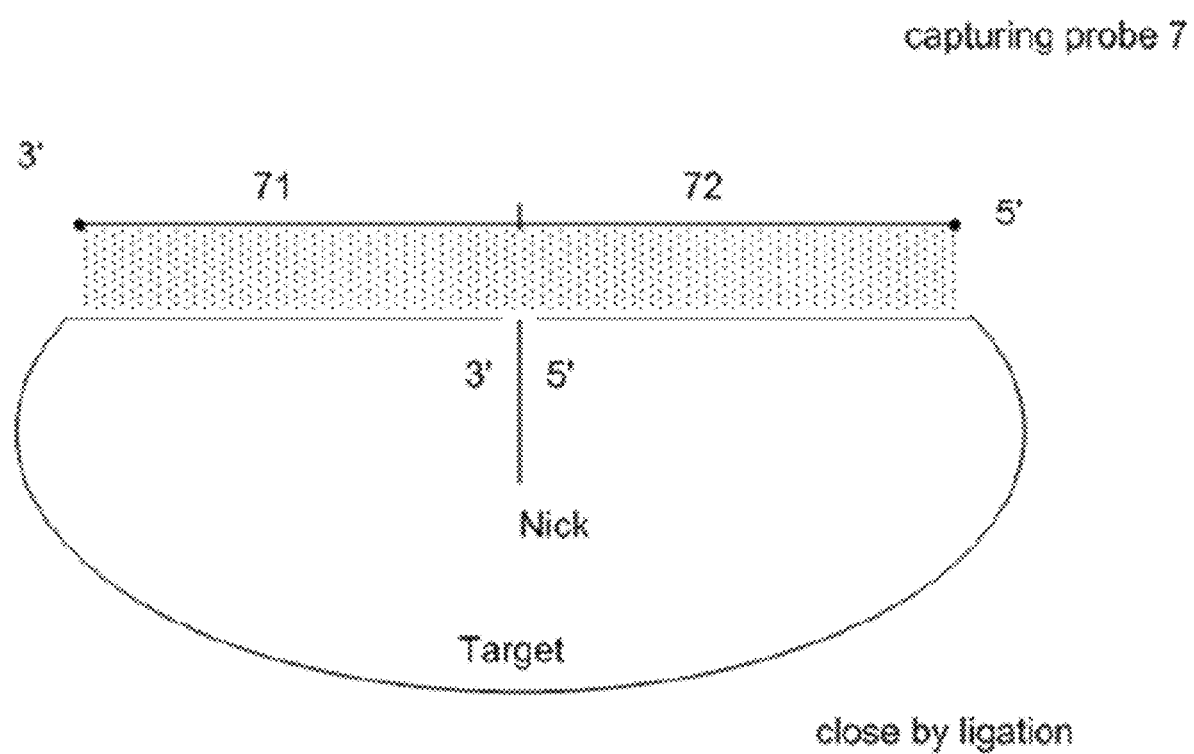

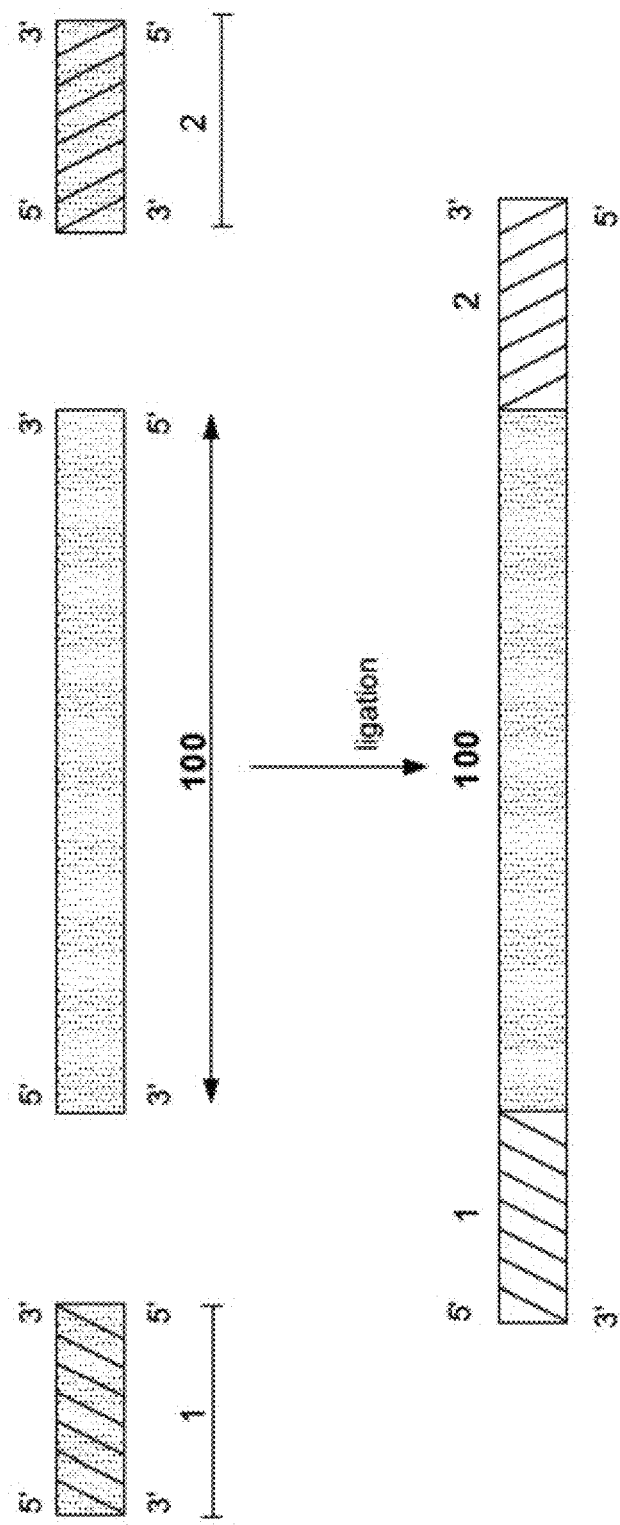

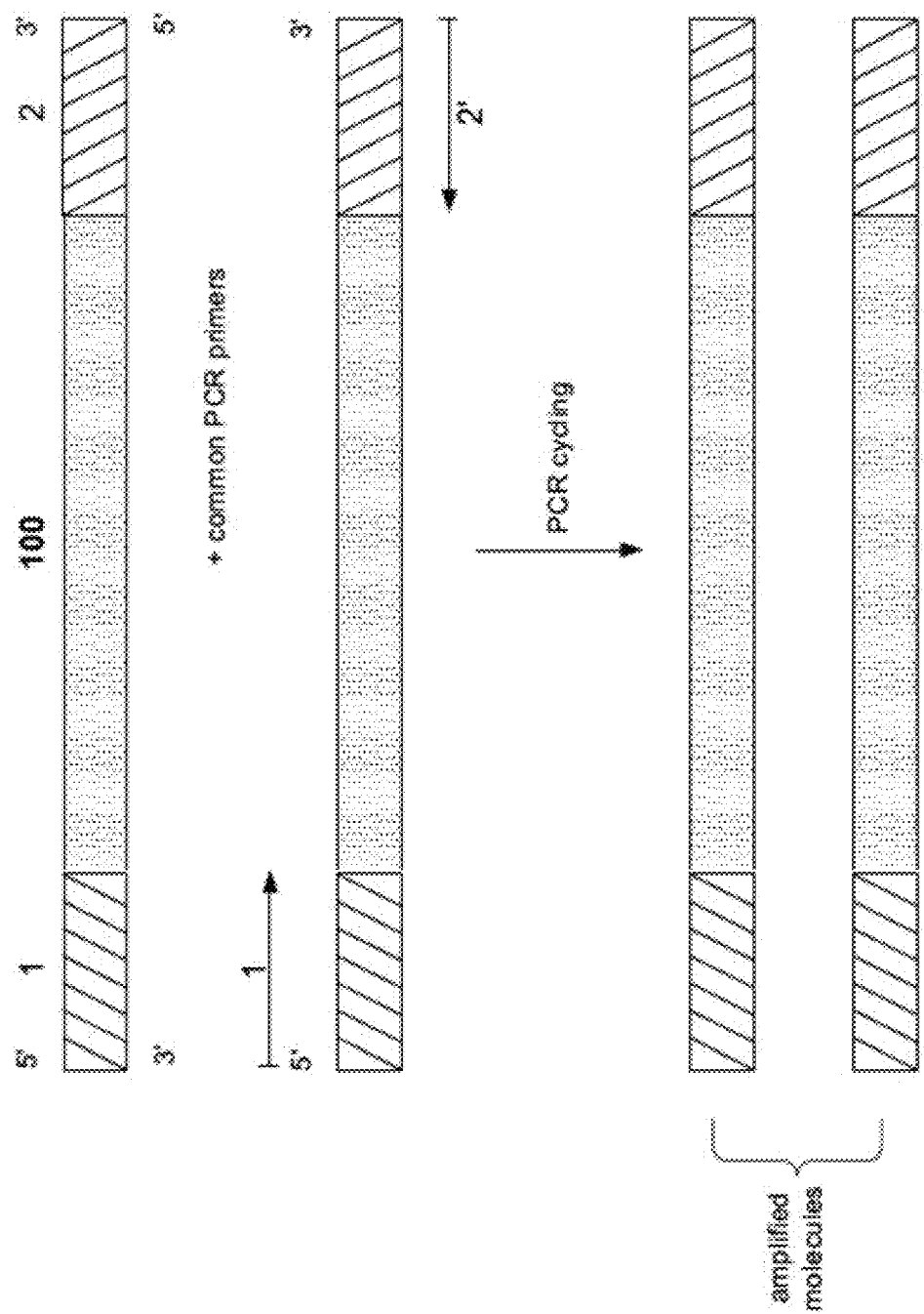

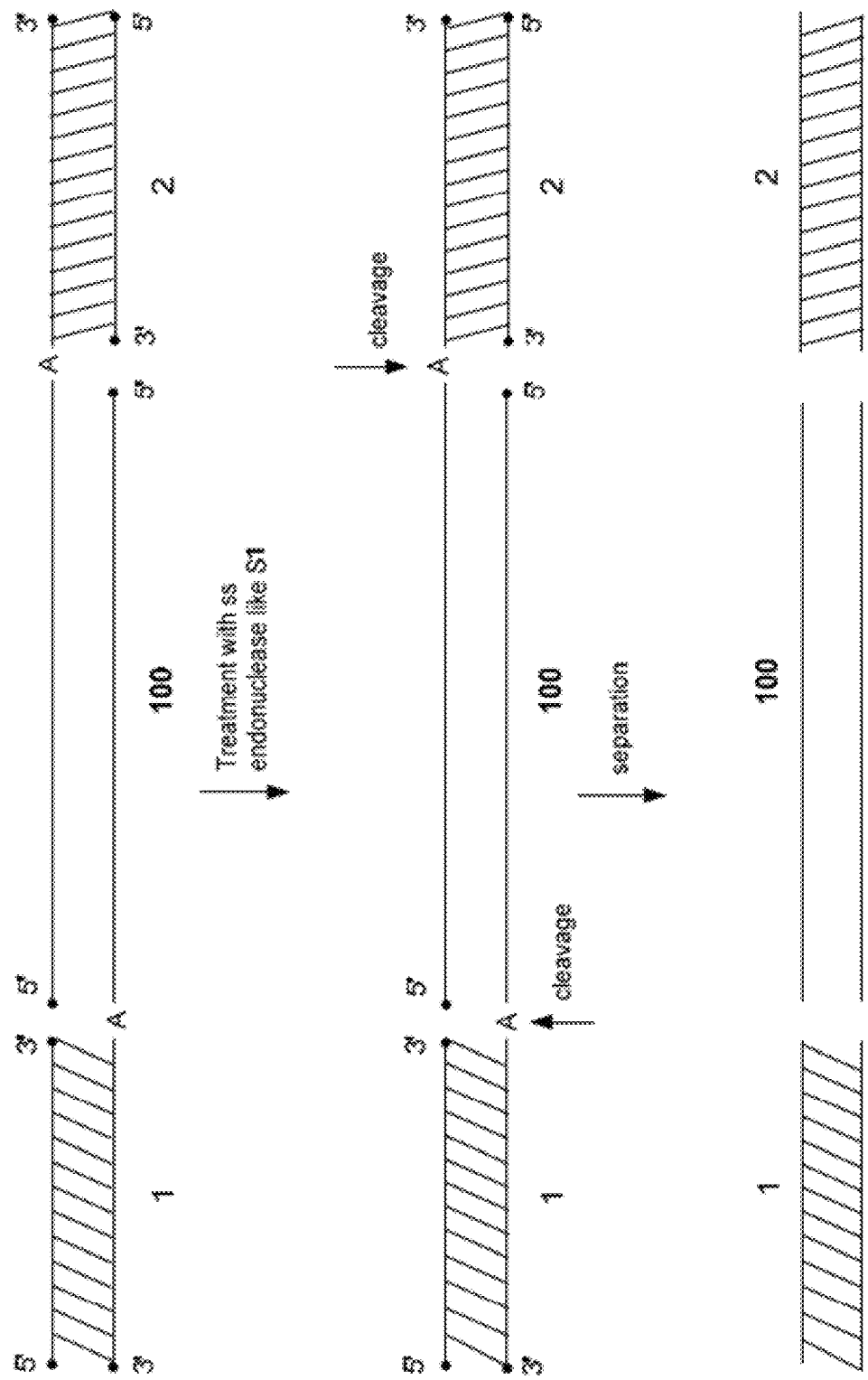

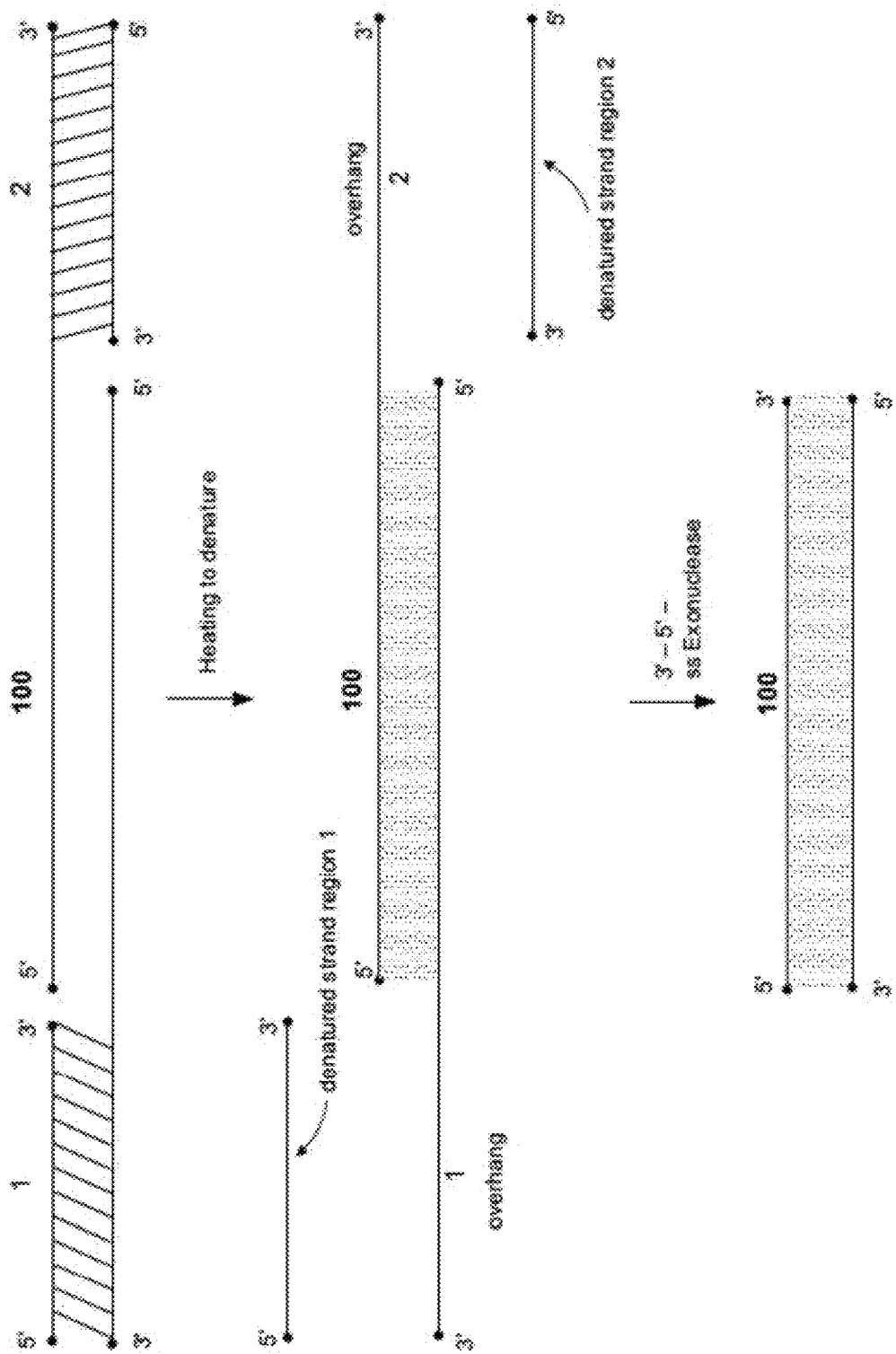

SEQUENCE LISTING

```
<160> NUMBER OF SEQ ID NOS: 5

<210> SEQ ID NO 1
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
acaatacctg gcggtgtgtc tgtgaggtct gaataaaaat taaatgcgca aaggcaggta      60
agatcctgag ctcagtgccc ggtgcacaga caccattgcg ggtgtggttc ctgtcattac     120
```

```
tcagggcctg ccctggtgtg tatgt                                            145

<210> SEQ ID NO 2
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
acaatacctg gcggtgtgtc tgtgaggtct gaataaaaat taaatgcgca aaggcaggta       60
agatcctgag ctcagtgccc ggtgcacaga caccattgcg ggtgtggttc ctgtcattac      120
tcagggcctg ccctggtgtg tatgtgactg catgtgtttg tgt                       163

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(12)
<223> OTHER INFORMATION: a, c, t, g, unknown or other

<400> SEQUENCE: 3
ggatgnnnnn nn                                                           12

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, c, t, g, unknown or other

<400> SEQUENCE: 4
nnnnnnnnnn catcc                                                        15

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: a, c, t, g, unknown or other

<400> SEQUENCE: 5
nnnnnnnnnn ncatcc                                                       16
```

METHODS OF ANALYZING NUCLEIC ACID FRAGMENTS

CROSS-REFERENCE

This application is a continuation of U.S. patent application Ser. No. 15/673,883, filed Aug. 10, 2017, which claims the benefit of U.S. Provisional Patent Application No. 62/373,332, filed Aug. 10, 2016, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Oct. 6, 2017, is named 50251-813_201_SL.txt and is 2,004 bytes in size.

BACKGROUND

Amplification of nucleic acids and analysis of the resulting amplification products are used in cloning, sequencing, genotyping, and gene expression. Multiple techniques for nucleic acids amplification have been developed, such as polymerase chain reaction (PCR), strand displacement amplification, and transcription-based amplification. Unfortunately, current methods are non-specific with respect to preserving the sequence information at the ends of nucleic acids. For example, in PCR, the binding of a forward and a reverse oligonucleotide to a target nucleic acid will produce an amplicon with a sequence corresponding to the sequence of the target nucleic acid between the forward and reverse oligonucleotides. In many instances, the forward and reverse oligonucleotides may bind at a region other than the end of the target nucleic acid, thereby producing an amplicon shorter than the target nucleic acid (e.g., losing the sequence information at the ends of the target nucleic acid). However, the sequence information at the ends of nucleic acid fragments (e.g., cell-free nucleic acid fragments) can be very useful in disease prognostics and diagnostics. Accordingly, the present disclosure provides methods for enriching and amplifying target nucleic acids in a sample while preserving the sequence information at the ends of the target nucleic acids.

Amplification of nucleic acids and subsequent analysis of the resulting amplification products (e.g., amplicons) can be performed in a number of molecular assays including molecular cloning, sequencing, genotyping, and gene expression. Amplification can be particularly useful where samples contain relatively small quantities of starting template material (e.g., nucleic acids). Multiple reports indicate that circulating cell-free DNA (cfDNA) in plasma can be non-randomly fragmented. Extremely low concentration of cfDNA in plasma (10-5000 genomes/ml) can make the study and detection of the fragmentation pattern difficult. While techniques such as whole genome amplification (WGA) have been developed to amplify small quantities of nucleic acids, the amplicons can be shorter than the template fragments from which the amplicons are produced. In some cases, nucleotides at the ends of the starting template nucleic acid fragments are not copied (e.g., these techniques can fail to preserve sequence information at the ends of template nucleic acid fragments), and are not useful for determining nucleic acid fragmentation patterns. The present disclosure provides compositions and the methods for the amplification of nucleic acid molecules (e.g., cell-free DNA molecules) while preserving sequence information at the ends of the molecules. Furthermore, the present disclosure provides embodiments for determining the nucleic acid fragmentation pattern following amplification where the sequence information at the ends of the nucleic acid molecules are preserved.

SUMMARY

In some aspects, the present disclosure provides methods that comprise identifying a nucleic acid fragmentation pattern in a subject by analyzing cell-free deoxyribonucleic acid (DNA) fragments in a biological sample from the subject. In some embodiments, the cell-free DNA fragments originating from normal cells and potentially from disease cells. In some embodiments, the method comprises obtaining the biological sample from the subject. In some embodiments, the method comprises enriching the biological sample. In some embodiments, the method comprises enriching the biological sample for a set of cell-free DNA fragments having ends that are mappable to one or more loci. In some embodiments, the one or more loci are associated with a disease. In some embodiments, the enriching comprises hybridizing at least one probe to each end of the cell-free DNA fragment. In some embodiments, the probe comprises a given sequence that is complementary to at least one end of the cell-free DNA fragment. In some embodiments, each nucleotide of the given sequence of the probe hybridizes with the cell-free DNA fragment. In some embodiments, the method comprises subjecting the set of enriched cell-free DNA fragments or derivatives thereof to sequencing to obtain a plurality of sequences. In some embodiments, the method comprises aligning the plurality of sequences to a reference to determine genomic positions for the plurality of sequences. In some embodiments, the genomic positions including positions corresponding to the ends of the cell-free DNA fragment. In some embodiments, the method comprises identifying a set of loci with specific fragmentation patterns in the plurality of sequences. In some embodiments, the set of loci correspond to the one or more loci associated with a disease. In some embodiments, the method comprises performing an enzymatic operation on the obtained biological sample. In some embodiments, sequencing the set of cell-free DNA fragments does not comprise a step of DNA amplification of the enriched cell-free DNA fragments. In some embodiments, identifying a set of loci comprises comparing the plurality of sequences to a reference genome to identify the set of loci with specific fragmentation patterns. In some embodiments, at each locus of the set of loci, a number of sequences having a sequence variant relative to the reference genome is above a threshold. In some embodiments, the disease is a tumor. In some embodiments, the disease cells comprise tumor cells. In some embodiments, the plurality of sequences is a plurality of sequence reads.

In some aspects, the present disclosure provides methods that comprise identifying a nucleic acid fragmentation pattern in a subject by analyzing cell-free deoxyribonucleic acid (DNA) fragments in a biological sample from the subject. In some embodiments, the cell-free DNA fragments originating from normal cells and potentially from disease cells. In some embodiments, the method comprises obtaining the biological sample from the subject. In some embodiments, the method comprises enriching by probe capture the biological sample for a set of cell-free DNA fragments having ends that are mappable to one or more loci. In some embodiments, the one or more loci are associated with a disease. In some embodiments, the enriching comprises hybridizing at least one probe to each end of the cell-free DNA fragment. In some embodiments, the probe comprises a given sequence that is complementary to at least one end of the cell-free DNA fragment. In some embodiments, each nucleotide of the given sequence of the probe hybridizes with the cell-free DNA fragment. In some embodiments, the method comprises identifying a set of loci with specific fragmentation patterns in the set of enriched cell-free DNA fragments. In some embodiments, the set of loci is identified by array hybridization. In some embodiments, the set of loci is identified by nucleic acid amplification. In some embodiments, the nucleic acid amplification includes polymerase chain reaction (PCR). In some embodiments, the disease is cancer.

In some aspects, the present disclosure provides methods that comprise amplifying cell-free nucleic acid molecules in a biological sample from the subject. In some embodiments, the method comprises ligating an adapter to each end of the cell-free nucleic acid molecules from a biological sample from the subject. In some embodiments, the adapter comprises a recognition sequence for a restriction endonuclease. In some embodiments, the restriction endonuclease is capable of cleaving at a junction between the adapter and the end of the cell-free nucleic acid molecule. In some embodiments, the method comprises amplifying the cell-free nucleic acid molecules comprising an adapter at each end using the adapter at each end of the cell-free nucleic acid molecules to generate amplified cell-free nucleic acid molecules comprising an adapter at each end. In some embodiments, the method comprises separating at least one adapter from at least one end of the amplified cell-free nucleic acid molecules comprising an adapter at each end using the restriction endonuclease. In some embodiments, the separating occurs at the junction between the adapter and the end of the cell-free nucleic acid molecule. In some embodiments, the cell-free nucleic acid molecules are double stranded. In some embodiments, the restriction endonuclease is a Type IIs nuclease. In some embodiments, the Type IIs nuclease is selected from the group consisting of BtsCI, FOKI, AP endonuclease, and Si endonuclease. In some embodiments, the concentration of the cell-free nucleic acid molecules in the sample is between about 10 and 10000 genomes per milliliter. In some embodiments, the biological sample is selected from the group consisting of whole blood, blood plasma, blood serum, urine, cerebrospinal fluid, buffy coat, and a combination thereof. In some embodiments, the method comprises repairing one or more ends of the cell-free nucleic acid molecules from the biological sample from the subject. In some embodiments, the repairing comprises blunting at least one of the one or more ends of the cell-free nucleic acid molecules to comprise at least one of a terminal 5'-phosphate group and a 3'-hydroxyl group. In some embodiments, the repairing further comprises attaching a deoxyadenosine nucleotide at the one or more ends of the cell-free nucleic acid molecules. In some embodiments, the adapter is double stranded. In some embodiments, the method comprises hybridizing at least one probe to each end of the amplified cell-free nucleic acid molecules. In some embodiments, the probe comprises a given sequence that is complementary to at least one end of the amplified cell-free nucleic acid molecules. In some embodiments, each nucleotide of the given sequence of the probe hybridizes with amplified cell-free nucleic acid molecules. In some embodiments, the method comprises subjecting the amplified cell-free nucleic acid molecules to sequencing. In some embodiments, the method comprises subjecting the amplified cell-free nucleic acid molecules to sequencing to obtain a plurality of sequences corresponding to the cell-free nucleic acid molecules. In some embodiments, the method comprises aligning the plurality of sequences to a reference genome. In some embodiments, the method comprises determining a set of genomic positions in the reference genome at which ends of the plurality of sequences occur at a rate above threshold, thereby determining a nucleic acid fragmentation pattern in the subject.

In some aspects, the present disclosure provides methods that comprise amplifying cell-free nucleic acid molecules in a biological sample from the subject. In some embodiments, the method comprises ligating an adapter to each end of the cell-free nucleic acid molecules from a biological sample from the subject. In some embodiments, an end of the adapter that is ligated to the cell-free nucleic acid molecules comprises an adenine base and a thymine base. In some embodiments, the method comprises amplifying the cell-free nucleic acid molecules comprising an adapter at each end using the adapter at each end of the cell-free nucleic acid molecules to generate amplified cell-free nucleic acid molecules comprising an adapter at each end. In some embodiments, an amplicon of the amplified cell-free nucleic acid molecule comprises one of a Uracil base, a Uridine base, and a Deoxyuridine base in the position of the thymine base. In some embodiments, the method comprises separating at least one adapter from at least one end of the amplified cell-free nucleic acid molecules comprising an adapter at each end using the restriction endonuclease. In some embodiments, the separating occurs at the junction between the adapter and the end of the cell-free nucleic acid molecule. In some embodiments, the method comprises treating the amplified cell-free nucleic acid molecules with Uracil-DNA Glycosylase (UDG), wherein the UDG treatment removes the one of the Uracil base, the Uridine base, and the Deoxyuridine base, thereby creating an apurinic/apyrimidinic (AP) site. In some embodiments, the amplifying comprises using one or more primers comprising one of a Uracil base, a Uridine base, and a Deoxyuridine base at a 3' end of the one or more primers. In some embodiments, the restriction endonuclease is an AP endonuclease, and the AP endonuclease generates a nick at the AP site. In some embodiments, the method comprises treating the plurality of cell-free nucleic acid molecules with an additional nuclease specific for single-stranded nucleic acids, thereby separating the adapter from the cell-free nucleic acid molecule at the cleavage site.

In some aspects, the present disclosure provides methods that comprise analyzing cell-free nucleic acid molecules in a biological sample from the subject. In some embodiments, the method comprises obtaining the biological sample from the subject. In some embodiments, the method comprises enriching by probe capture the biological sample for a set of cell-free nucleic acid fragments having ends that are mappable to one or more loci. In some embodiments, the one or more loci are associated with a disease. In some embodiments, the enriching comprises hybridizing a probe to each end of the cell-free nucleic acid fragment. In some embodiments, the probe comprises a first sequence that is complementary to a first end of the cell-free nucleic acid fragment and a second sequence that is complementary to a second end of the cell-free nucleic acid fragment. In some embodiments, the first sequence and the second sequence are separated by a third sequence. In some embodiments, the method comprises ligating the first end of the cell-free nucleic acid molecule to the second end of the cell-free nucleic acid molecule, thereby forming a circularized cell-free nucleic acid molecule comprising a sequence corresponding to the third sequence. In some embodiments, the method comprises determining an amount of the circularized cell-free nucleic acid molecule in said biological sample. In some embodiments, at least two of the set of cell-free nucleic acid molecules are different lengths. In some embodiments, the method comprises extending the first end of the cell-free nucleic acid molecule to the second end of the cell-free nucleic acid molecule. In some embodiments, the ligating is performed using a ligase. In some embodiments, the method comprises amplifying the circularized cell-free nucleic acid molecule. In some embodiments, the amplifying comprises performing rolling-circle amplification. In some embodiments, the determining comprises performing quantitative polymerase chain reaction (PCR). In some embodiments, the disease is cancer.

In some aspects, the present disclosure provides a nucleic acid probe. In some embodiments, the nucleic acid probe comprises a first probe sequence along a 3' end of the nucleic acid probe. In some embodiments, the first probe sequence is at least partially complementary to a first target sequence along a 3' end of a target nucleic acid. In some embodiments, the nucleic acid probe comprises a second probe sequence along a 5' end of the nucleic acid probe. In some embodiments, the second probe sequence is at least partially complementary to a second target sequence along a 5' end of the target nucleic acid. In some embodiments, the nucleic acid probe comprises a third probe sequence between the first and the second probe sequence. In some embodiments, the nucleic acid probe is capable of enriching for ends of cell-free nucleic acid molecules at an enrichment efficiency of at least 80% as compared to other regions of the cell-free nucleic acid molecules. In some embodiments, the enrichment efficiency is at least 90%. In some embodiments, the enrichment efficiency is at least 95%. In some embodiments, the enrichment efficiency is at least 98%. In some embodiments, at least one of the first probe sequence and the second probe sequence are mappable to one or more loci associated with a disease. In some embodiments, the disease is cancer.

In some aspects, the present disclosure provides kits for analyzing cell-free nucleic acid molecules in a biological sample from a subject. In some embodiments, the kit comprises one or more nucleic acid probes. In some embodiments, the kit comprises instructions for directing a subject to use the nucleic acid probe set to analyze the cell-free nucleic acid molecules in the biological sample from the subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which some of the principles of the invention are utilized, and the accompanying drawings of which:

FIGS. 1A-C illustrate the denaturation of a target nucleic acid fragment, and some embodiments of how the probes (e.g., capturing probes) may hybridize to each end of the nucleic acid fragment;

FIGS. 3A-B illustrate the hybridization of single stranded ligation probe or probes to a capturing probe hybridized to either end of a target nucleic acid strand, and the enzymatic ligation of the ligation probe to the target nucleic acid strand;

FIGS. 7A-C illustrate the hybridization of a (A-B) a single capturing probe or (C) a two part capturing probe (e.g., two probes) to a target nucleic acid strand, wherein one part of the capturing probe comprises two regions complementary to the ends of the target nucleic acid, wherein hybridization of the ends of the target nucleic acid to the capturing probe causes the target nucleic acid to form a nucleic acid loop.

FIGS. 8A-B illustrate an embodiment of the present disclosure wherein adapters are ligated to each blunt end of a nucleic acid fragment, and primers are hybridized to the adapters to amplify the nucleic acid fragment.

FIG. 11 illustrates another embodiment of the present disclosure wherein, following treatment with an AP endonuclease to generate a nick at an AP site and heating to denature the strands, a nuclease specific for single stranded nucleic acids is used to separate the remaining single stranded portion of the adapter from the nucleic acid fragment.

DETAILED DESCRIPTION

Figure 1A:
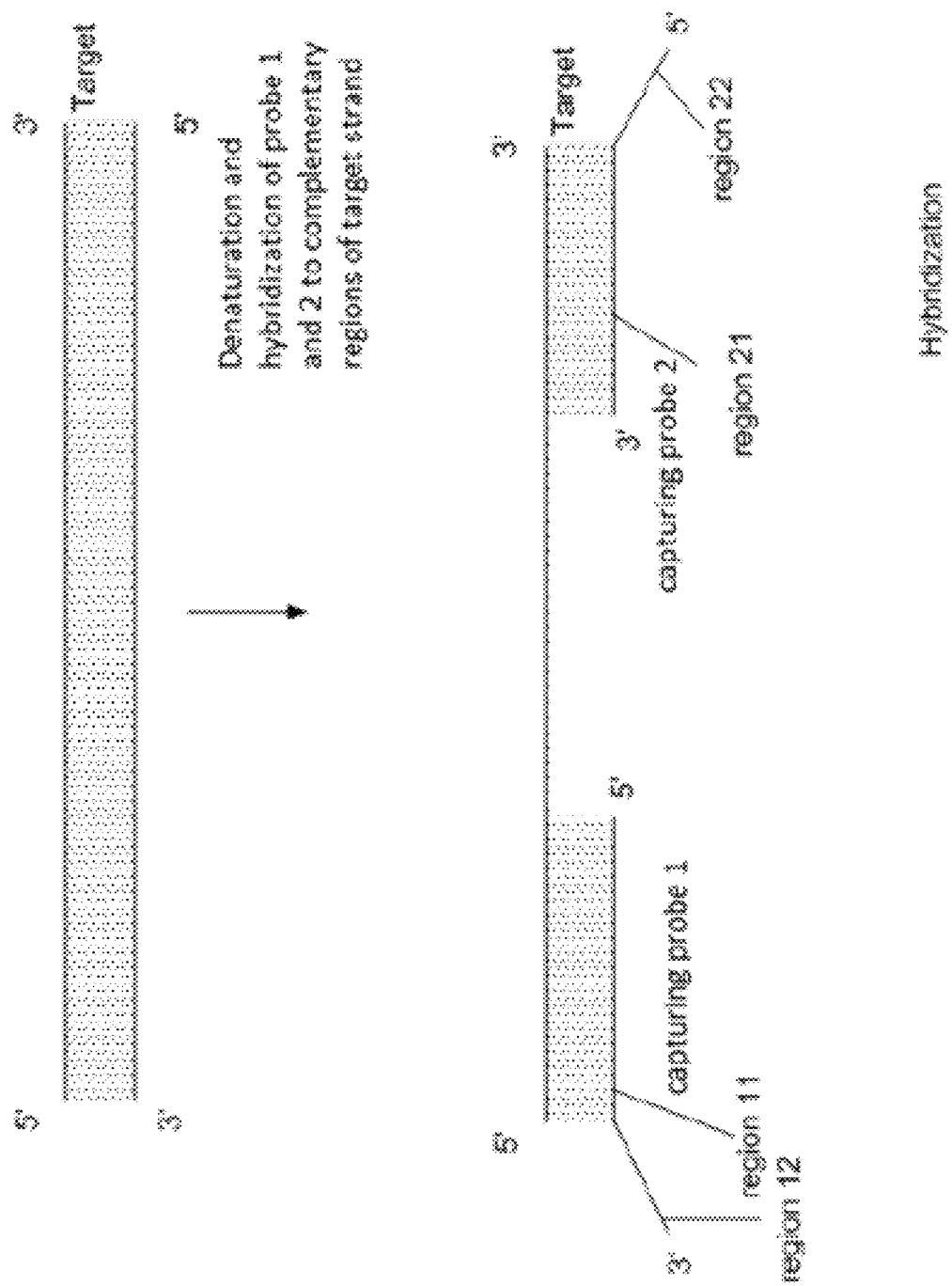

Generally, embodiments of the present disclosure are related to methods for selectively enriching and/or amplifying a sample for target nucleic acids while preserving the sequence information of one or more ends of the target nucleic acid. The present disclosure also provides computer software products and systems for selective enrichment and/or amplification of target nucleic acids while preserving the sequence information of one or more ends of the target nucleic acid.

Several aspects are described below with reference to example applications for illustration. It should be understood that numerous specific details, relationships, and methods are set forth to provide a full understanding of the features described herein. It will be apparent to one having ordinary skill in the art that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" can mean within an acceptable error range for the particular value as determined by one of ordinary skill in the art, which will depend in part on how the value is measured or determined, i.e. the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed. The term "about" has the meaning as commonly understood by one of ordinary skill in the art. In some embodiments, the term "about" refers to ±10%. In some embodiments, the term "about" refers to ±5%.

The terms "attach", "bind", "couple", and "link" can be used interchangeably and can refer to covalent interactions (e.g., by chemically coupling), or non-covalent interactions (e.g., ionic interactions, hydrophobic interactions, hydrogen bonds, hybridization, etc.).

The terms "specific", "specifically", or specificity" can refer to the preferential recognition, contact, and formation of a stable complex between a first molecule and a second molecule compared to that of the first molecule with any one of a plurality of other molecules (e.g., substantially less to no recognition, contact, or formation of a stable complex between the first molecule and any one of the plurality of other molecules). For example, two molecules may be specifically attached, specifically bound, specifically coupled, or specifically linked. For example, specific hybridization between a first nucleic acid and a second nucleic acid can refer to the binding, duplexing, or hybridizing of the first nucleic acid preferentially to a particular nucleotide sequence of the second nucleic acid under stringent conditions. A sufficient number complementary base pairs in a nucleic acid sequence may be required to specifically hybridize with a target nucleic acid sequence. A high degree of complementarity may be needed for specificity and sensitivity involving hybridization, although it need not be 100%.

The term "cancer" as used herein may refer to a hyperproliferation of cells, unregulated cell growth, lack of differentiation, local tissue invasion, cell dysplasia (e.g., a change in cell shape, number, size or pigmentation), or cell metastasis. Non-limiting examples of cancer include adrenal cancer, anal cancer, basal cell carcinoma, bile duct cancer, bladder cancer, cancer of the blood, bone cancer, a brain tumor, breast cancer, bronchus cancer, cancer of the cardiovascular system, cervical cancer, colon cancer, colorectal cancer, cancer of the digestive system, cancer of the endocrine system, endometrial cancer, esophageal cancer, eye cancer, gallbladder cancer, a gastrointestinal tumor, kidney cancer, hematopoietic malignancy, laryngeal cancer, leukemia, liver cancer, lung cancer, lymphoma, melanoma, mesothelioma, cancer of the muscular system, Myelodysplastic Syndrome (MDS), myeloma, nasal cavity cancer, nasopharyngeal cancer, cancer of the nervous system, cancer of the lymphatic system, oral cancer, oropharyngeal cancer, osteosarcoma, ovarian cancer, pancreatic cancer, penile cancer, pituitary tumors, prostate cancer, rectal cancer, renal pelvis cancer, cancer of the reproductive system, cancer of the respiratory system, sarcoma, salivary gland cancer, skeletal system cancer, skin cancer, small intestine cancer, stomach cancer, testicular cancer, throat cancer, thymus cancer, thyroid cancer, a tumor, cancer of the urinary system, uterine cancer, vaginal cancer, or vulvar cancer. The term 'lymphoma' may refer to any type of lymphoma including B-cell lymphoma (e.g., diffuse large B-cell lymphoma, follicular lymphoma, small lymphocytic lymphoma, mantle cell lymphoma, marginal zone B-cell lymphoma, Burkitt lymphoma, lymphoplasmacytic lymphoma, hairy cell leukemia, or primary central nervous system lymphoma) or a T-cell lymphoma (e.g., precursor T-lymphoblastic lymphoma, or peripheral T-cell lymphoma). The term 'leukemia' may refer to any type of leukemia including acute leukemia or chronic leukemia. Types of leukemia include acute myeloid leukemia, chronic myeloid leukemia, acute lymphocytic leukemia, acute undifferentiated leukemia, or chronic lymphocytic leukemia. In some cases, the cancer patient does not have a particular type of cancer. For example, in some instances, the patient may have a cancer that is not breast cancer. Examples of cancer may include cancers that cause solid tumors as well as cancers that do not cause solid tumors. Furthermore, any of the cancers mentioned herein may be a primary cancer (e.g., a cancer that is named after the part of the body where it first started to grow) or a secondary or metastatic cancer (e.g., a cancer that has originated from another part of the body).

The term "sample", "biological sample" or "subject sample" is meant to include any tissue or material derived from a living or dead subject. A biological sample may be a cell-free sample. A biological sample generally comprises a nucleic acid (e.g., DNA or RNA) or a fragment thereof. The nucleic acid in the sample may be a cell-free nucleic acid. A sample may be a liquid sample or a solid sample (e.g., a cell or tissue sample). The biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. Stool samples can also be used. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). The biological sample may be treated to physically disrupt tissue or cell structure (e.g., centrifugation and/or cell lysis), thus releasing intracellular components into a solution which may further contain enzymes, buffers, salts, detergents, and the like which are used to prepare the sample for analysis.

The methods disclosed herein are generally useful for analyzing and/or enriching nucleic acids (e.g., circulating and/or cell-free DNA fragments). A person of skill in the art will appreciate that a nucleic acid can generally refer to a substance whose molecules consist of many nucleotides linked in a long chain. Non-limiting examples of the nucleic acid include an artificial nucleic acid analog (e.g., a peptide nucleic acid, a morpholino oligomer, a locked nucleic acid, a glycol nucleic acid, or a threose nucleic acid), chromatin, niRNA, cDNA, DNA, single stranded DNA, double stranded DNA, genomic DNA, plasmid DNA, or RNA. In some embodiments, nucleic acid can be double stranded or single stranded. In some embodiments, a sample can comprise a nucleic acid, and the nucleic acid can be intracellular. In some embodiments, a sample can comprise a nucleic acid, and the nucleic acid can be extracellular (e.g., cell-free). In some embodiments, a sample can comprise a nucleic acid (e.g. chromatin), and the nucleic acid can be fragmented.

Samples may be enriched by any amount. For example, a method of the present disclosure may be used to enrich one or more nucleic acids within a sample by 50% (e.g., the enrichment efficiency may be about 50%, resulting in the concentration of the one or more nucleic acids in the sample increasing by about 50%). The enrichment efficiency for any methods of the present disclosure may be less than about 1%, about 1%, about 2%, about 3%, about 4%, about 5%, about 10%, about 15%, about 20%, about 25%, about 30%, about 40%, about 50%, about 60%, about 70%, about 80%, about 90%, about 100%, or greater than about 100%. In some embodiments, the enrichment efficiency may fall within a range. For example, the enrichment efficiency for a method of the present disclosure may be between about 10% and about 40%.

In some embodiments, methods of the present disclosure comprise use of one or more probes (e.g., capturing probes and ligation probes) and/or adapters. Generally, a probe or an adapter may be single stranded or double stranded. A probe or an adapter may be a polynucleotide comprising one or more barcodes, primer binding sites, and/or cleavage sites. A probe may be used to target and/or bind to a nucleic acid of interest, and may be used in a subsequent enrichment step to enrich a sample for the target nucleic acid. In some embodiments, a method of the present disclosure may comprise a first probe (e.g., a capturing probe) that associates or binds to a second probe (e.g., a ligation probe). For example, a method of the present disclosure may comprise a capturing probe binding to a target nucleic acid, thereby generating a complex between the nucleic acid and the capturing probe with a sticky end overhang. A ligation probe may then be used to bind to sticky end overhang of the capturing probe. Any of the probes or adapters of the present disclosure may be associated with or coupled to a solid support or extraction moiety that can be used to enrich the target nucleic acid in the sample. In another example, a method of the present disclosure can comprise a double stranded adapter binding to each blunt end of a target nucleic acid. The adapters can subsequently be used to amplify the target nucleic acid.

A barcode sequence can generally refer to a series of nucleotides that allows for the unique identification of the corresponding probe. A barcode sequence can have any number of nucleotides. In some embodiments, a barcode can comprise less than about 10 nucleotides. In some embodiments, a barcode can comprise about 10 nucleotides. In some embodiments, a barcode can comprise about 20 nucleotides. In some embodiments, a barcode can comprise about 30 nucleotides. In some embodiments, a barcode can comprise about 40 nucleotides. In some embodiments, a barcode can comprise about 50 nucleotides. In some embodiments, a barcode can comprise about 75 nucleotides. In some embodiments, a barcode can comprise at least about 100 nucleotides. In some embodiments, a barcode can comprise at least about 500 nucleotides. In some embodiments, a barcode can comprise between about 5 and about 15 nucleotides. In some embodiments, a barcode can comprise between about 15 and about 50 nucleotides. In some embodiments, a barcode can comprise between about 50 and about 100 nucleotides. For example, a barcode can comprise about 15 nucleotides. In another example, a barcode sequence can comprise between about 50 nucleotides and about 75 nucleotides.

Generally, a primer binding site can be a region of a nucleic acid where a single-stranded oligonucleotide binds to initiate replication. In some embodiments comprising a double stranded nucleic acid, the primer binding site can be on one of two complementary strands (e.g., the strand to be copied). A primer binding site can comprise any number of nucleotides. In some embodiments, the primer binding site can comprise about 1 to about 50 nucleotides. In some embodiments, the primer binding site can comprise about 18 to about 22 nucleotides. In some embodiments, the GC content (e.g., the number of guanine and cytosine nucleotides as a percentage of the total number of nucleotides in the primer binding site) can be about 30% to 70%. In some embodiments, the GC content can be less than 40%. In some embodiments, the GC content can be greater than 60%.

A cleavage site can generally refer to a specific nucleotide sequence at which site-specific molecules (e.g., proteases, endonucleases, or enzymes) can cut a polynucleotide. In one example, cleaving the polynucleotide at the cleavage site releases the target nucleic acid from the polynucleotide (e.g., a capturing probe, a ligation probe, and/or an adapter). A recognition site can generally refer to a specific nucleotide sequence on a polynucleotide that site-specific molecules (e.g., proteases, endonucleases, or enzymes) recognize in order to cut the polynucleotide. In one example, cleaving the polynucleotide at the cleavage site releases the target nucleic acid from the polynucleotide (e.g., a capturing probe, a ligation probe, and/or an adapter). In some embodiments, a site at which a nuclease cuts a polynucleotide may occur outside of the recognition site of the nuclease. For example, Type IIs restriction endonucleases may be used to cut a polynucleotide outside of the recognition sequence of the Type IIs restriction endonuclease. In some embodiments, the cleavage site can comprise at least one endonuclease recognition site. In some embodiments, the endonuclease recognition site can comprise a Type I endonuclease recognition site, a Type II endonuclease recognition site, a Type IIS endonuclease recognition site, a Type IIP endonuclease recognition site, a Type IIC endonuclease recognition site, a Type IIT endonuclease recognition site, a Type III endonuclease recognition site, a Type IV endonuclease recognition site, or a Type V endonuclease recognition site. Non-limiting examples of endonuclease recognition sites include an AatII recognition site, an Acc65I recognition site, an AccI recognition site, an AclI recognition site, an AatII recognition site, an Acc65I recognition site, an AccI recognition site, an AclI recognition site, an AcuI recognition site, an AfeI recognition site, an AflII recognition site, an AgeI recognition site, an AlwI recognition site, an ApaI recognition site, an ApaLI recognition site, an ApoI recognition site, an AscI recognition site, an AseI recognition site, an AsiSI recognition site, an AvrII recognition site, a BaeI recognition site, a BamHI recognition site, a BbsI recognition site, a BbsI-HF recognition site, a BbvI recognition site, a BccI recognition site, a BceAI recognition site, a BcgI recognition site, a BciVI recognition site, a BclI recognition site, a BclVI recognition site, a BcoDI recognition site, a BfuAI recognition site, a BglII recognition site, a Bme1580I recognition site, a BmrI recognition site, a BmtI recognition site, a BpmI recognition site, a BpuEI recognition site, a BsaI recognition site, a BsaI-HF recognition site, a BsaHI recognition site, a BsaXI recognition site, a BseRI recognition site, a BsgI recognition site, a BsiEI recognition site, a BsiWI recognition site, a BsmAI recognition site, a BsmBI recognition site, a BsmFI recognition site, a BsmI recognition site, a BspCNI recognition site, a BspMI recognition site, a BspQI recognition site, a BspEI recognition site, a BspHI recognition site, a BsrDI recognition site, a BsrI recognition site, a BsrGI recognition site, a BssHII recognition site, a BstBI recognition site, a BstZ17I recognition site, a BtgI recognition site, a BtgZI recognition site, a BtsCI recognition site, a BtsI recognition site, a BtsIMutI recognition site, a ClaI recognition site, a CspCI recognition site, a DraI recognition site, an EaeI recognition site, an EagI recognition site, an EarI recognition site, and EciI recognition site, an EcoRI recognition site, an EcoRV recognition site, an FauI recognition site, a FokI recognition site, an FseI recognition site, an FspI recognition site, an HaeII recognition site, an HgaI recognition site, an HincII recognition site, a HindIII recognition site, an HpaI recognition site, an HphI recognition site, an HpyAV recognition site, a KasI recognition site, a KpnI recognition site, an MboII recognition site, an MfeI recognition site, an MluI recognition site, an MlyI recognition site, an MmeI recognition site, an MnlI recognition site, an MscI recognition site, an MspA1I recognition site, an MfeI recognition site, an MluI recognition site, an MscI recognition site, an MspA1I recognition site, an NaeI recognition site, a NarI recognition site, an NcoI recognition site, an NdeI recognition site, an NgoMIV recognition site, an NheI recognition site, an NmeAIII recognition site, a NotI recognition site, an NruI recognition site, an NsiI recognition site, an NspI recognition site, a PacI recognition site, a PciI recognition site, a PleI recognition site, a PmeI recognition site, a PmlI recognition site, a PsiI recognition site, a PspOMI recognition site, a PstI recognition site, a PvuI recognition site, a PvuII recognition site, a SacI recognition site, a SacII recognition site, a SalI recognition site, a SapI recognition site, an SbfI recognition site, an ScaI recognition site, an SfaNI recognition site, an SfcI recognition site, an SfoI recognition site, an SgrAI recognition site, an SmaI recognition site, an SmlI recognition site, an SnaBI recognition site, an SpeI recognition site, an SphI recognition site, an SspI recognition site, an StuI recognition site, an SwaI recognition site, an XbaI recognition site, an XhoI recognition site, and an XmaI recognition site. In a particular example, the cleavage site can comprise NotI endonuclease recognition site.

In some embodiments, binding of a probe to a target nucleic acid may form a double stranded DNA (e.g., duplex complex). In some embodiments, the entire target nucleic acid strand may bind to the probe (e.g., resulting in a DNA molecule that is double stranded over the length of the target nucleic acid strand). In some instances, not all of the nucleotides of the target nucleic acid may hybridize with the probe, resulting in the formation of secondary nucleic acid structures (e.g., hairpins, single-nucleotide bulges, multi-nucleotide bulges, or loops). A hairpin structure may occur when two regions of the target nucleic acid strand, which are substantially complementary in nucleotide sequence when read in opposite directions, base-pair to form a double helix that ends in an unpaired loop. A single-nucleotide bulge or a multi-nucleotide bulge may occur when two strands that are substantially, but not completely, complementary form a duplex complex, resulting in a single-nucleotide or multi-nucleotide bulge at the position of the nucleotide(s) that is (are) non-complementary. A nucleic acid loop may generally refer to a complex wherein the 5' and 3' ends of a nucleic acid strand are directly coupled (e.g., by ligation of the 5' end to the 3' end) or indirectly coupled (e.g., by hybridizing the 5' end of a nucleic acid with the 5' end of a probe, and the 3' end of the nucleic acid with the 3' end of the probe).

Cell-Free DNA for Disease Screening

Disease cells can release nucleic acid fragments into the circulatory system of a subject. For example, tumors may release fragments of tumor-derived DNA into the circulatory system (Bettegowda, et al. 'Detection of Circulating Tumor DNA in Early- and Late-Stage Human Malignancies.' *Sci. Trans. Med.,* 2014, pp. 1-25). The detection of mutations among cell-free nucleic acids in plasma, serum, and the other body fluids is attractive for the development of cancer screening tests because they can provide access to the tumor-associated genetic and genomic changes relatively noninvasively and in lieu of the direct assessment of a tumor biopsy. All forms of genetic and genomic changes associated with tumor, cancers, or malignancies can be detected among the cell-free nucleic acid population. Examples of cancer-associated changes or cancer-specific changes are provided herein. Cancer-specific can generally refer to a change that comes from a cancer cell, and cancer-associated can mean the change can come from a cancer cell, or a premalignant lesion, or other tissues due to anatomical proximity, physiological association, developmental association or a reaction to the presence of the cancer. A test for the screening of many different cancers with high clinical sensitivity and specificity can detect a wide range and large number of mutations.

It is contemplated that the methods of the present disclosure may be used to detect non-tumor derived nucleic acids. For example, the methods of the present disclosure may be used to detect and/or enrich for fetus-derived nucleic acids. Detecting fetus-derived nucleic acids can be useful for a variety of reasons, such as detecting abnormal chromosome number, determining gender detection, or identifying paternally inherited disorders. Aneuploidy is an abnormal chromosome number, typically characterized by the presence of an extra copy of a single chromosome or the absence of one copy of a single chromosome. For example, trisomy 21 is the presence of an extra copy of chromosome 21 and can cause Down syndrome. The gender of the fetus can be determined by detecting and/or enriching for nucleic acid fragments derived from the Y chromosome. Similarly, if a father is affected by a genetic condition, methods of the present disclosure may be used to enrich for the cell-free fetal DNA (e.g., from the Y chromosome) and can be analyzed for the presence of a specific mutation related to the condition. In another example, a ratio of fetal-derived DNA to maternal DNA may be used, e.g., to determine a stage of pregnancy.

In another example, the methods of the present disclosure may also be used to detect nucleic acids derived from transplanted tissue. As cells undergo apoptosis, cell-derived DNA can be deposited into the blood stream. Accordingly, increasing concentrations of transplant tissue-derived DNA can indicate the rejection of a transplanted tissue. In some cases, the methods of the present disclosure may be used to monitor the rejection of a transplant tissue in a subject.

Test Sensitivity (e.g., Breadth and Depth)

To achieve the same sensitivity as the plasma EBV DNA test for NPC detection (Chan et al. Cancer 2013; 119: 1838-1844), a test can detect at least ~500 copies of plasma DNA bearing a cancer-associated change in order to achieve the detection of the equivalent DNA content of one tumor cell in the circulation. This can be achieved either by detecting 500 copies of one tumor-associated change, such as in the case of the plasma EBV DNA test, or one copy each of 500 different tumor-associated mutations, or a combination, namely multiple copies of a set of <500 mutations. Plasma DNA fragments can be generally <200 bp in length. Detection of any one cancer-associated change can involve the detection of one plasma DNA fragment bearing such a change, termed an informative cancer DNA fragment.

Breadth

Cancers can be highly heterogeneous. The mutation profile can vary greatly between cancers of different organs, vary greatly between different subjects with cancers of the same organ or even between different tumor foci in the same organ of the same subject (Gerlinger et al N Engl J Med 2012; 366: 883-892). In some cases, any one tumor-associated mutation is positive in a small subset of any cancer subject. For example, the Catalogue of Somatic Mutations in Cancer (COSMIC) database documents the range of genetic mutations that have been detected in tumor tissues.

A plasma DNA test for cancer detection or primary screening can scout through a much wider search space within the genome in order to collect enough mutations (e.g., copy number aberrations and sequence variants relative to a reference genome, such as a constitutional genome, parental genome, human genome or a variant thereof) or other cancer-specific or cancer-associated changes (e.g., methylation changes) to make up the sum of 500 cancer-specific plasma DNA fragments per cancer cell. In some cases, the chance of any one well-documented cancer-associated mutation occurring in any one tumor can be 1%. In such cases, a test can target the detection of 50,000 putative mutation sites in order to have at least 500 mutations detected per tumor (based on Poisson probability distribution). 500,000 putative mutations or cancer-associated changes can be tested in order to have at least 5,000 mutations or cancer-associated changes represented for any one tumor. In some cases, the chance of any one well-documented cancer-associated mutations or changes occurring in any one tumor can be 0.1%. In such cases, then 50,000 mutations or changes can be tested in order to have at least 50 mutations or changes represented for any one tumor.

The test can achieve a broad survey of plasma DNA fragments in a sample in order to identify enough fragments bearing any one type of cancer-associated change or mutation. The breadth of the survey can be achieved with the use of genome wide approaches or targeted approaches that cover a large fraction of the genome, for example enough to cover at least 50,000 targets.

Depth

Multiple plasma DNA fragments that bear a mutation can be detected to reach a specified threshold, e.g., 500 informative cancer DNA fragments for each genome-equivalent of cancer cell. For example, if only one mutation is identified in a particular tumor, then 500 plasma DNA fragments covering that mutation can be used. If 50 different mutations are present in the tumor, on average, at least 10 informative cancer DNA fragments covering each one of those 50 mutations can be detected.

Tumor DNA can represent a minor DNA population in plasma. Some cancer-associated changes can be heterozygous in nature (e.g., with one change per diploid genome). To detect 10 copies of informative cancer DNA fragment (i.e. plasma DNA fragments that carry at least one cancer-associated change) per locus, at least 100 molecules from the locus in a plasma sample with 20% tumor DNA fraction can be analyzed. The ability to detect multiple plasma DNA fragments covering any single mutation site can be dependent on how deep the plasma sample is surveyed. There can be a finite number of cancer cell genomes in the plasma sample, which can affect both the depth and breadth of the plasma DNA analysis.

A test or protocol can detect a tumor fraction of 1% in a sample. There can be 1,000 genome-equivalents of DNA in every milliliter of plasma, so there can be 10 cancer cell-equivalent of DNA in a milliliter sample with 1% tumor DNA fraction. Every single cancer-specific DNA fragment in the sample can be detected, and 10 genome-equivalents of any one cancer-associated change can be available for detection. Targeted detection can provide a signal of 10 genome-equivalents. In some cases, this may lack the analytical sensitivity for robust detection of a cancer at 1% fractional concentration. If the mutation detected is heterozygous, there can be 5 plasma DNA fragments showing this mutation.

With 1% tumor DNA fraction, the depth of the analysis at this mutation site can be at least 1,000 times to be able to detect the 10 genome-equivalents of plasma DNA with the mutation. In this situation, the breadth of the analysis can make up for the relatively low number of copies detected per mutation site. In some cases, the selective detection of a handful or even just hundreds of mutation sites can achieve the sensitivity required for a screening test to detect early cancer.

In some cases, there can be loss or reduction in plasma DNA templates and informative cancer DNA fragments during the sample processing steps, DNA sequencing library preparation steps, and probe based target capture hybridization process. Some steps may introduce biases in the relative proportions among different mutations and between the cancer and non-cancer derived DNA. For example, in some cases, PCR amplification of target sequencing libraries, genomic DNA sequencing libraries, and amplicon sequencing can introduce GC biases as well as create PCR duplicates. For massively parallel DNA sequencing, errors in the identification of a sequenced fragment can result from sequencing errors arisen during PCR amplification or during the sequencing, during base-calling, or due to alignment errors. The signal detection mechanism of the analysis platform may have a detection limit before a confident positive readout can be provided for the detection of a mutation (e.g., 5 mutant fragments might be needed for a detectable signal).

The number of somatic mutations harbored by a malignant tumor can range between about 1,000 to several 10,000s (see e.g., Lawrence et al. Nature 2013; 499: 214-218). In some cases, depending on the fractional concentration of tumor DNA in the plasma sample, one can have enough informative cancer DNA fragments in the plasma sample (in some cases, <10 milliliters plasma can be obtained per blood draw) to achieve early noninvasive cancer detection.

In some cases, the cancer information content that can be obtained in each plasma sample can be maximized, e.g., to attain sensitivity for cancer screening. Provided herein are processes that can enrich samples for target nucleic acids of interest (e.g., tumor-derived nucleic acids) while preserving sequence information at one or both ends of the nucleic acid. In this application, described are methods for amplifying nucleic acid fragments in a sample while preserving the sequence information at one or both ends of the nucleic acid fragment. Some embodiments of the present disclosure can enrich the biological sample for informative cancer DNA fragments by using a probe (e.g., a capturing probe) to bind to at least one end of a DNA fragment of interest. Increasing the concentration the target nucleic acids of interest in a sample (e.g., tumor derived DNA) can help achieve clinical sensitivity and specificity for a cancer screening test. In various embodiments, ultra-deep and broad sequencing, exhaustive, or total template sequencing is performed. PCR-free massively parallel sequencing may be performed to increase the cost-effectiveness of the ultra-deep and broad sequencing, exhaustive, or total template sequencing. The ultra-deep and broad sequencing, exhaustive, or total template sequencing can be achieved through single molecule sequencing.

Targeted Enrichment

The present disclosure comprises methods for the selective attachment of probes to the ends of target nucleic acids such that they can be amplified in one or more multiplex reactions by PCR or other amplification methods.

The methods disclosed herein are generally useful for analyzing nucleic acids (e.g., cell-free DNA fragments). Non-limiting examples of the nucleic acid include an artificial nucleic acid analog (e.g., a peptide nucleic acid, a morpholino oligomer, a locked nucleic acid, a glycol nucleic acid, or a threose nucleic acid), chromatin, niRNA, DNA, cDNA, circulating DNA, cell-free DNA or RNA, single stranded DNA or RNA, double stranded DNA or RNA, genomic DNA, plasmid DNA, or RNA (e.g., mRNA, tRNA, etc.). In some embodiments, nucleic acid can be double stranded or single stranded. In some embodiments, a sample can comprise a nucleic acid, and the nucleic acid can be intracellular. In some embodiments, a sample can comprise a nucleic acid, and the nucleic acid can be extracellular (e.g., cell-free). In some embodiments, a sample can comprise a nucleic acid (e.g. genomic DNA), and the nucleic acid can be fragmented.

Target nucleic acids may be treated to repair the ends of the target nucleic acid molecules. Double stranded DNA fragmented by nebulization, acoustic shearing, or nucleases can be repaired. For example, damaged double stranded DNA can be converted by a mixture of polymerase and phosphatase to blunt ended DNA having 5'-phosphates and 3'-hydroxyl.

Different types of 3' or 5' end damage can be repaired. For example, 3' or 5' end damage can be repaired by treatment with one or more exonucleases such that damaged nucleotides at the end of the strand are removed by degradation. Damaged nucleotides at the end of the target nucleic acid can be removed by applying enzymatic treatment with one or more AP endonucleases involved in the DNA base excision repair pathway.

In some embodiments, DNA end repair end can be intentionally omitted, e.g., to ensure that only target nucleic acids with DNA ends generated by natural DNA cleavage during apoptosis are analyzed. Mechanically fragmented DNA molecules can contain damaged and non-ligatable ends, and in some cases mechanically fragmented DNA molecules with damaged or non-ligatable ends are not be able to effectively used for end 3' or 5' end joining.

An enrichment step for specific nucleic acids can be used. For example, mixtures containing RNA, single stranded (ss) and double stranded (ds) DNA molecules can be enriched for RNA, ss, or dsDNA only by using different techniques. RNA molecules can be degraded by RNase without affecting DNA molecules. Ss and ds DNA molecules can be also be degraded by ss or ds DNA specific exonucleases. In some instances, this step can be performed first followed by an end repair step.

A method provided herein can comprise hybridizing at least one probe on an end, or to each end, of a target nucleic acid (see e.g., FIG. 1A). In the first step, oligonucleotide capturing probes 1 and 2 are annealed to the 3' and 5' ends of the single strand specific sequence of interest. Capturing probe 1 includes at least one complementary region 11 and second non-complementary region 12. In an annealing step, the 5' end (e.g., one or more nucleotides at the 5' end) of a target nucleic acid hybridizes to the 5' end (e.g., one or more nucleotides at the 5' end) of the capturing probe at complementary region 11. The complementary region may comprise any number of nucleotides. For example, an the complementary region can comprise at least about 1, 2, 3, 4, 5, 6, 7, 8, 9, 10, 15, 20, 30, 40, 50, 75, 100, or more nucleotides. In some embodiments, the complementary region comprises about 10 to about 25 nucleotides. The length and sequence can be chosen to confer stability and specificity of hybridization to the template. Region 12 can form an overhanging 3' end containing sequence which is non complementary to sequence of the target nucleic acid. The non-complementary region can comprise any number of nucleotides. For example, a non-complementary region can comprise at least about 1, 2, 3, 4, 5, 6, 7, 8, 9, 10, 15, 20, 30, 40, 50, 75, 100 or more nucleotides. In some embodiments, the non-complementary region comprises about 2 to about 25 nucleotides.

In some embodiments, the junction between region 11 and 12 is designed so that the 5' end of the target forms the perfectly matched position to the junction in the duplex complex between target and capturing probe 1 (FIG. 1B). If the position of the target at the 5' end is longer by several nucleotides, the 5' end of the target will be mismatched with the nucleotides of the non-complementary sequence of region 12. If the 5' end of the target nucleic acid is shorter by several nucleotides a gap of un-annealed sequence will be formed next to the annealed 5' end of the probe (FIG. 1B).

In some embodiments, the capturing probe 2 includes a complementary region 21 and a second non-complementary region 22 (FIG. 1C). In an annealing step, the 3' end of sequence of interest hybridizes to the 3' end of the capturing probe at complementary region 21. The complementary region may comprise any number of nucleotides. For example, an the complementary region can comprise at least about 1, 2, 3, 4, 5, 6, 7, 8, 9, 10, 15, 20, 30, 40, 50 or more nucleotides. In some embodiments, the complementary region comprises about 10 to about 25 nucleotides. The length and sequence can be chosen to confer stability and specificity of hybridization to the template. Region 21 can form an overhanging 5' end containing sequence which is non complementary to sequence of the target nucleic acid. The non-complementary region may comprise any number of nucleotides. For example, an the non-complementary region can comprise at least about 1, 2, 3, 4, 5, 6, 7, 8, 9, 10, 15, 20, 30, 40, 50 or more nucleotides. In some embodiments, the non-complementary region comprises about 2 to 25 nucleotides.

In some embodiments, the junction between region 21 and 22 is designed such that the 3' end of the target nucleic acid forms a complete duplex complex. If the position of target at 3' end is longer by several nucleotides, the 3' end of the target will be mismatched with the nucleotides of the non-complementary sequence of region 12 (FIG. 1C). If the 3' end of the target nucleic acid is shorter by several nucleotides a gap of un-annealed sequence in region 21 will formed next to annealed 3' end (FIG. 1C).

Figure 2A:
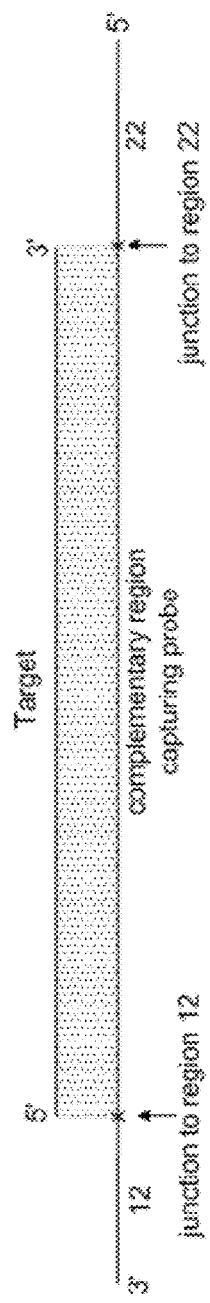
FIG. 2A illustrates the hybridization of a single capturing probe to one strand of a target nucleic acid, wherein the single capturing probe is longer than the target nucleic acid and comprises a substantially or partially complementary sequence to the target nucleic acid strand.
Figure 2B:
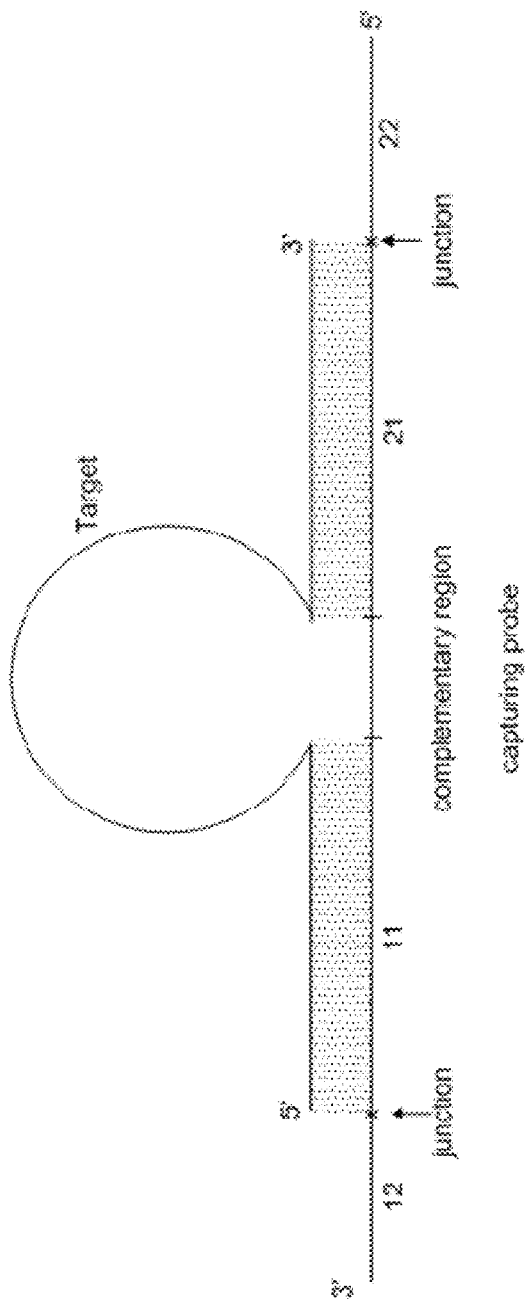
FIG. 2B illustrates the hybridization of a single capturing probe to a target nucleic acid strand, wherein the capturing probe comprises a region complementary to the ends of the target nucleic acid, wherein hybridization of the ends of the target nucleic acid to the capturing probe causes the target nucleic acid to form a nucleic acid loop.

In another embodiment illustrated in FIG. 2A, the capturing probe may comprise a sequence corresponding to the entire sequence of the target nucleic acid. In some instances, the capturing probe may be longer than the target nucleic acid, and comprise overhangs or uncomplementary regions (e.g., regions 12 or 22) at one or both ends of the probe adjacent to the region complementary to the target nucleic acid. In some embodiments, a nucleic acid can comprise a single stranded overhang at one or more ends of the nucleic acid. In some embodiments, the overhang can occur on the 3' end of a nucleic acid. In some embodiments, the overhang can occur on the 5' end of a nucleic acid. An overhang can comprise any number of nucleotides. For example, an overhang can comprise at least about 1, 2, 3, 4, 5, 6, 7, 8, 9, 10, 15, 20, 30, 40, 50 or more nucleotides. Also, the complementary region of the capturing probe may contain two or more complementary sequences joined into one sequence as long as the complementary region 11 and 21 at 5' and 3' ends form a complex with the target molecule. Non-complementary regions 12 and 22 can be joined at the 3' or 5' ends of the complementary regions of the capturing probe. During hybridization unpaired nucleotides of either the target nucleic acid or the probe can form a loop or bulge out of unpaired nucleotides (FIG. 2B).

Figure 3A:
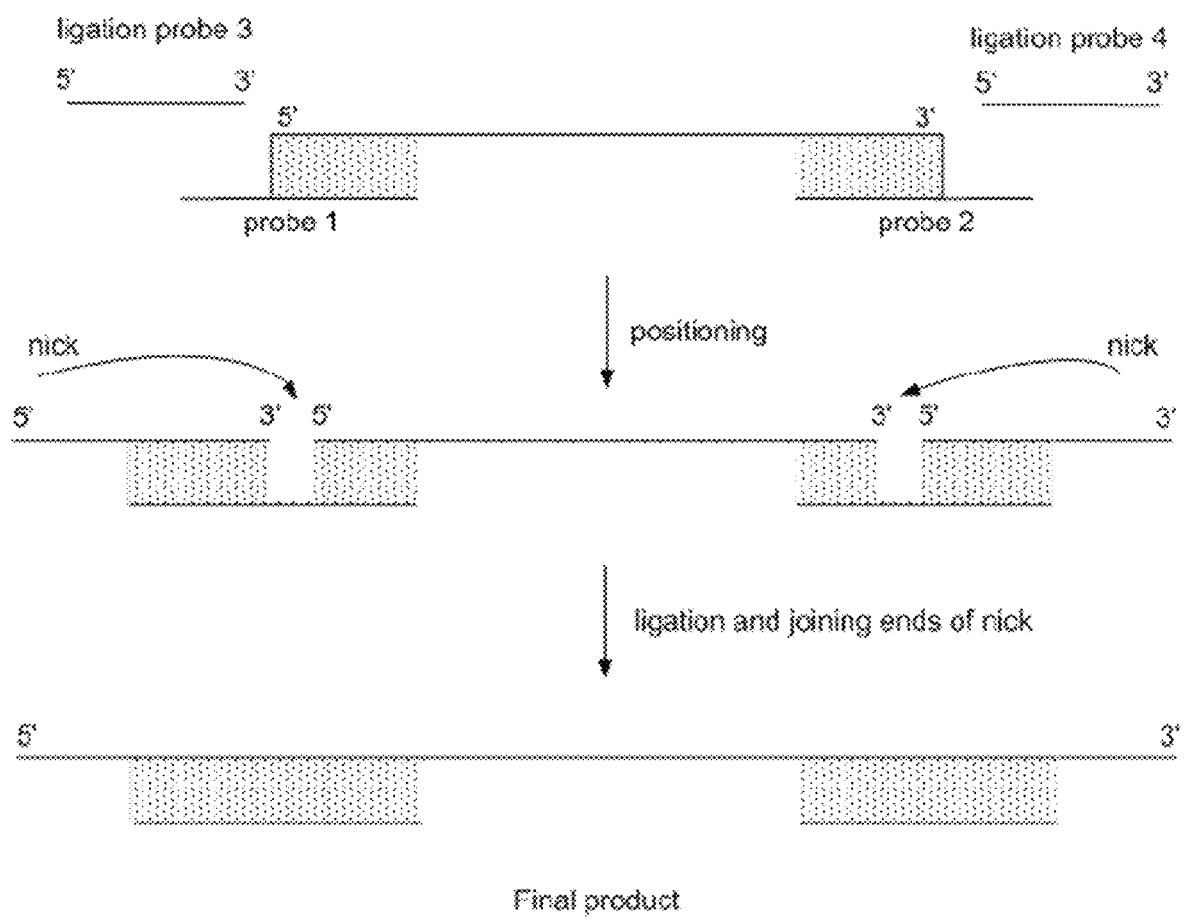

In some embodiments, a method comprising hybridization between a capturing probe and a target (FIG. 3A) may also comprise the addition of ligation probes 3 and 4 to the complex formed by the target nucleic acid and capturing probes 1 and 2. Ligation probes can have complementary sequences at the ends which can form a stable duplex or transient complex with the rest of the complex for a ligation reaction. During enzymatic ligation reaction the nick can be closed by joining the 5' and 3' end of the target and ligation probes forming a continuous sequence. Perfectly paired ends on the complex can be effectively ligated. In some cases, any mismatched nucleic acids at the ends or gap structures will not able to complete ligation and will not form the continuous molecule between ligation probe 3, target sequence, and ligation probe 4.

FIG. 3B illustrates a composition comprising ligation of probe 3 and probe 4 to the target nucleic acid. The ligation probe 3 can be designed to include at least one region 31 which is complementary to region 12 of capturing probe 1 and can support ligation between 3' end of the ligation probe and 5' end of the target sequence. The length of the region 31 may be, for example between about 2 and about 25 bps. Completely matched sequences of regions 12 and 31 can support joining ends between 3' and 5' ends. In some cases, any mismatched, unannealed 5' end, or gap at 5' end of the target will not able to support efficient ligation to 3' end of ligation probe.

In some embodiments, ligation probe 4 can be preferably designed to include at least one region 41 which is complementary to region 22 of probe 2 and can support ligation between 5' end of the ligation probe and 3' end of the target sequence. The length of the region 41 may be, for example between about 2 and about 25 nucleotides. In some embodiments, only completely matched sequences of regions 22 and 41 will able to support joining ends between 3' and 5' ends. In some cases, any mismatched or unannealed 3' end of the target, or gap at 3' end the target may not able to support efficient ligation to the 5' end of ligation probe 4. After ligation completely matched 5' and 3' end of the target will be jointed to the ligation probes 3 and 4 into one continues sequence. Additional regions can be added to the ligation probe for subsequent use. Regions 33 and 43 can be used as common or specific primer for PCR amplification of final ligation product. Regions 32 and 42 can be used for barcoding sequences if multiple target need to be detected.

Figure 4A:
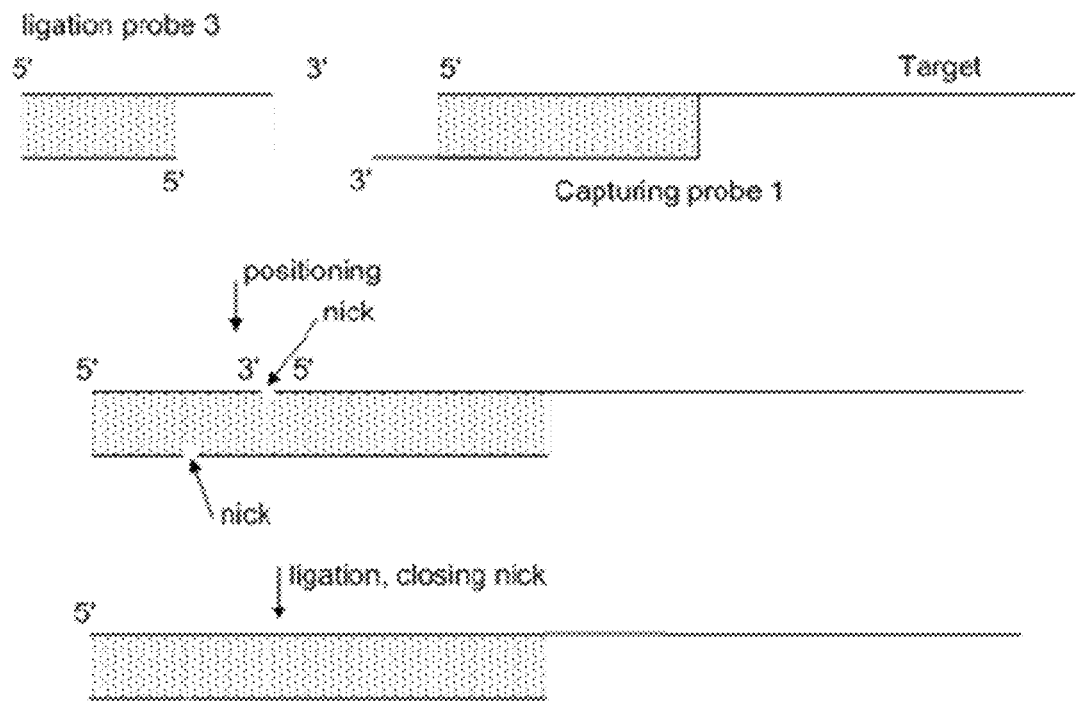
FIGS. 4A-B illustrate the hybridization of double stranded ligation probe or probes to a capturing probe hybridized to either end of a target nucleic acid strand, wherein the double stranded ligation probe comprises a sticky end overhang that is substantially complementary to at least a portion of the capturing probe that is non-complementary to the end of the target nucleic acid strand.
Figure 4B:
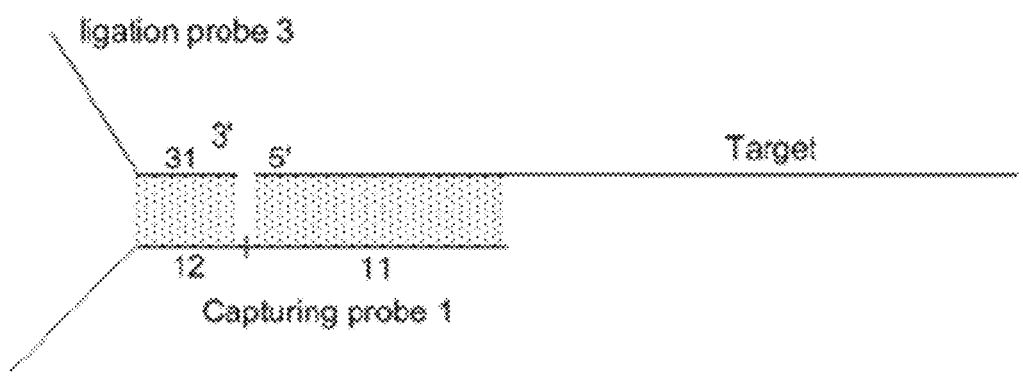
Figure 4C:
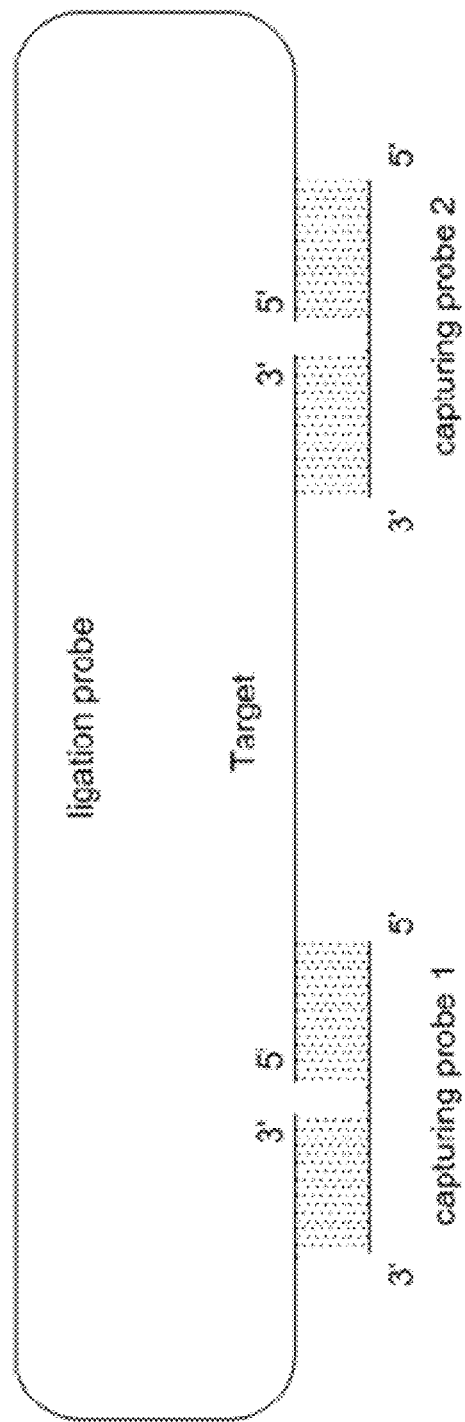
FIG. 4C illustrates the hybridization of a single ligation probe to capturing probes hybridized to both ends of a target nucleic acid strand, thereby forming a loop comprising the target nucleic acid and the ligation probe.

In another embodiment, different modifications of ligation probes are presented in FIG. 4A, the ligation probe can be double stranded with corresponding overhanging end so it can form perfectly matched double stranded complex containing nicks with overhanging end of the target. After ligation nick will be closed and ligation probe strand will be joined to target sequence. Also ligation probe may have partial complementary region to the overhanging ends of the capturing probe as long the length of the complementary end will support ligation. See FIG. 4B for illustration of ligation probe 3 containing region 31 which is partially complementary to the region 12 of the capturing probe 1. Same type or mixed type of ligation probes can be used to attach to 5' and 3 end of the target sequence by joining ends. Ligation probes can be part of the one continuous molecule like molecular inversion probe (MIP) and produce the circular molecules after completion of the ligation reaction (FIG. 4C).

Appending of ligation probe to target sequence can be performed for single or multiple target ligations (FIG. 3B). In one embodiment for each specific target, target specific capturing probe set can be designed. Region 11 and 21 can be target specific but regions 12 and 22 can be common between all targets. In this case common ligation probes 3 and 4 can be used for ligation with multiple targets.

In another embodiment the capturing probes are target specific. Also target specific ligation probe regions 31 and 41 can be designed to match the corresponding capturing probe regions 12 and 22. But common sequence can be used for regions 33 and 43 so multiplex PCR amplification can be performed with common PCR primers.

Figure 5A:
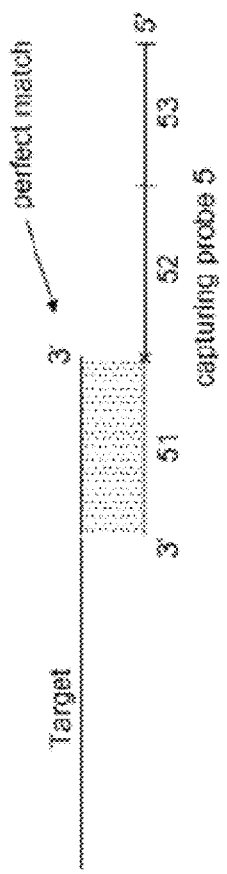
FIGS. 5A-C illustrate some embodiments of how a capturing probe may hybridize to at least one 3' end of a target nucleic acid strand, and conditions under which DNA synthesis may occur to extend the 3' end of the target nucleic acid strand.

In another aspect illustrated in FIG. 5A, after a first step of hybridization between target sequence and capturing probes, two mixed enzymatic reactions can be used in second step. A ligation probe can be used to append to the 5' end of the target sequence by ligation as described above. The 3' end of the target molecule will be extended by polymerase reaction copying the sequence from the capturing probe 5. Both enzymatic reactions: i) appending a ligation probe at 5' end of the target by ligation (not shown); and ii) polymerase extension of the 3' end of the target using capturing probe 5 as template, can be performed simultaneously or separately.

FIG. 5A illustrates one embodiment comprising the capturing probe 5 used for extension of the 3' end of the target nucleic acid. Probe 5 contains at least one region that is complementary to 3' end of the target sequence. Region 51 is selected to be complementary to the target nucleic acid over a length that may be, for example, about 10 to 25 nucleotides. The length and sequence are chosen to confer stability and specificity of hybridization to the template. Capturing probe may also contain additional regions. Region 53 at the 5' end can be used as primer binding site for PCR amplification. Region 52 may comprise a barcode. A barcode sequence can generally refer to a series of nucleotides that allows for the unique identification of the corresponding probe. A barcode sequence can have any number of nucleotides. A barcode can comprise any number of polynucleotides. In some embodiments, a barcode can comprise less than about 10 nucleotides. In some embodiments, a barcode can comprise at least about 10 nucleotides. In some embodiments, a barcode can comprise at least about 20 nucleotides. In some embodiments, a barcode can comprise at least about 30 nucleotides. In some embodiments, a barcode can comprise at least about 40 nucleotides. In some embodiments, a barcode can comprise at least about 50 nucleotides. In some embodiments, a barcode can comprise at least about 75 nucleotides. In some embodiments, a barcode can comprise at least about 100 nucleotides. In some embodiments, a barcode can comprise at least about 500 nucleotides. In some embodiments, a barcode can comprise at least about 1000 nucleotides. In some embodiments, a barcode can comprise between about 5 and about 50 nucleotides. In some embodiments, a barcode can comprise between about 50 and about 100 nucleotides. In some embodiments, a barcode can comprise between about 100 and about 150 nucleotides. For example, a probe can comprise a tag, and the tag can comprise a 20 nucleotide barcode. In another example, a barcode sequence can comprise between about 50 nucleotides and about 75 nucleotides.

Figure 5B:
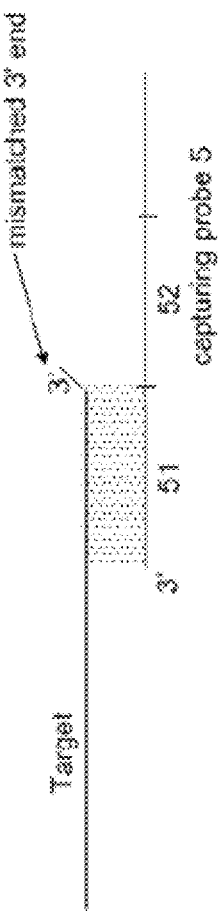

If the position of the 3' end of the target nucleic acid is moved due to extra nucleotides at the 3' end, the resulting complex between the target and capturing probe may have a mismatched 3' end (FIG. 5B). DNA polymerases without 3'-5' exonuclease activities may be used to prevent extending any mismatched 3' end (FIG. 5B).

If the position of the 3' end of the target nucleic acid is moved relative to region 51 of capturing probe 5 such that it forms a gap (e.g., the 3' end of the target does not match the 5' end of region 51), the gap (e.g., unannealed sequence of region 51) can be filled by 3' extension. If target is shorter at the 3' end and size of the gap exceeds the length of capturing sequence 51 (e.g., the target does not bind to the capturing probe), a product may not be formed. If the size of the gap is small and leftover sequence at the 3' end of the target is capable forming a complex with region 51 of the capturing probe, then the 3' end may be extended.

Figure 5C:
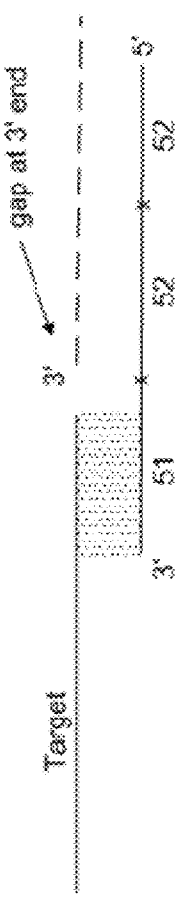

In another embodiment if the position of 3' end of the target nucleic acid is not clearly defined the capturing probe 5 can be intentionally designed with a gap such that any possible 3' position can be extended (FIG. 5C).

Figure 6:
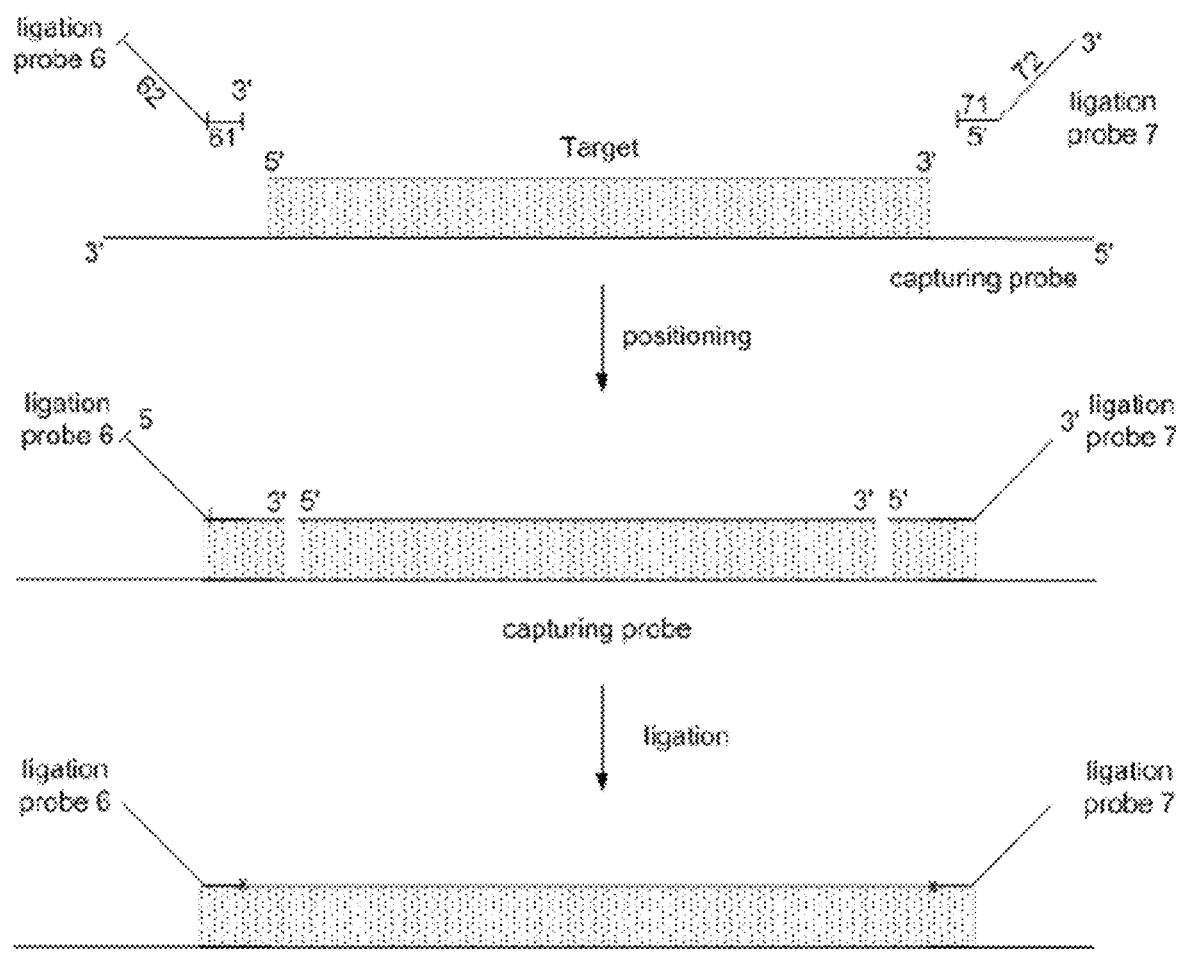
FIG. 6 illustrates the hybridization of ligation probes to a capturing probe at a region of the capturing probe that is adjacent to a region that is complementary to a target nucleic acid strand, and ligation of the ligation probes to the target nucleic acid strand.

In another aspect illustrated in FIG. 6, when the position of the 5' or 3' ends of the target is not clearly defined or multiple position of 5' and 3' ends are present in different targets, a larger capturing probe may be used for first step of annealing. The sequence of the capturing can cover the area of possible end position with the sequence of the capturing probe larger than largest expected size of the target of interest or far most position of either 3' or 5' end of the target of interest.

In another embodiment, a capturing probe may not need to contain contiguous complementary sequence of the target and may contain only sequence complementary to the 5' and the 3' end of the target, so that a loop structure is formed during hybridization.

In another embodiment, ligation probes 6 and 7 may be added to a complex formed between the target nucleic acid and the capturing probe. Ligation probe 6 contains region 61 at 3' end. This region may be between about 2 and about 15 nucleotides, and comprise all possible combinations of nucleotide compositions or random composition at the 5' end. During annealing, ligation probe 6 can form a transient complementary complex at the 5' end of the target nucleic acid and a ligase can join the 3' end of ligation probe 6 to the 5' end of the target molecule. A person having skill in the art will appreciate that a variety of ligases may be used to complete ligation with transiently stable duplex structures of only several nucleotides in length. Similarly, ligation probe 7 contains region 71 at the 5' end. This region may comprise between about 2 and about 15 nucleotides and contain all possible combinations of nucleotide compositions or random composition at 3' end. During annealing/positioning correct or proper sequence composition of ligation probe 7 can form complementary complex at the 3' end of the target. A ligase may be used to ligate the ligation probe 7 to the 3' end of the target nucleic acid. Probes 6 and 7 can contain regions 62 and 72 that can be used as PCR primer sites and used as common PCR primers. In mixtures of multiple targets with several end positions, NGS sequencing may permit deconvolution of the 5' and 3' ends positions for each individual target nucleic acid.

Figure 7B:
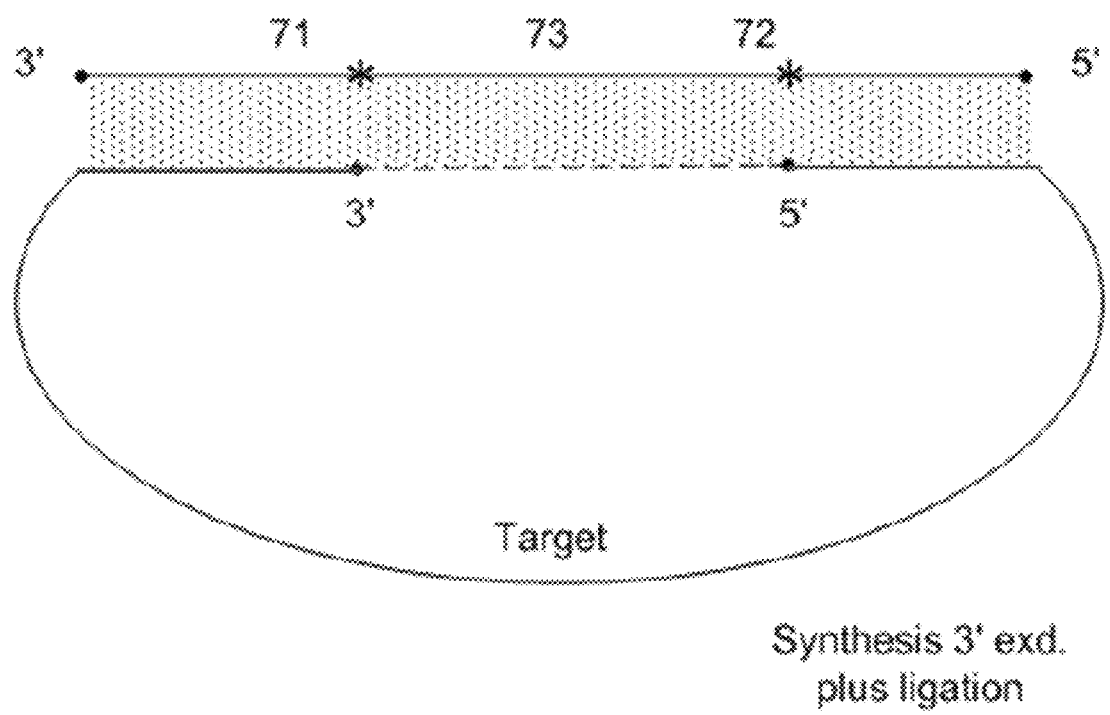
Figure 7C:
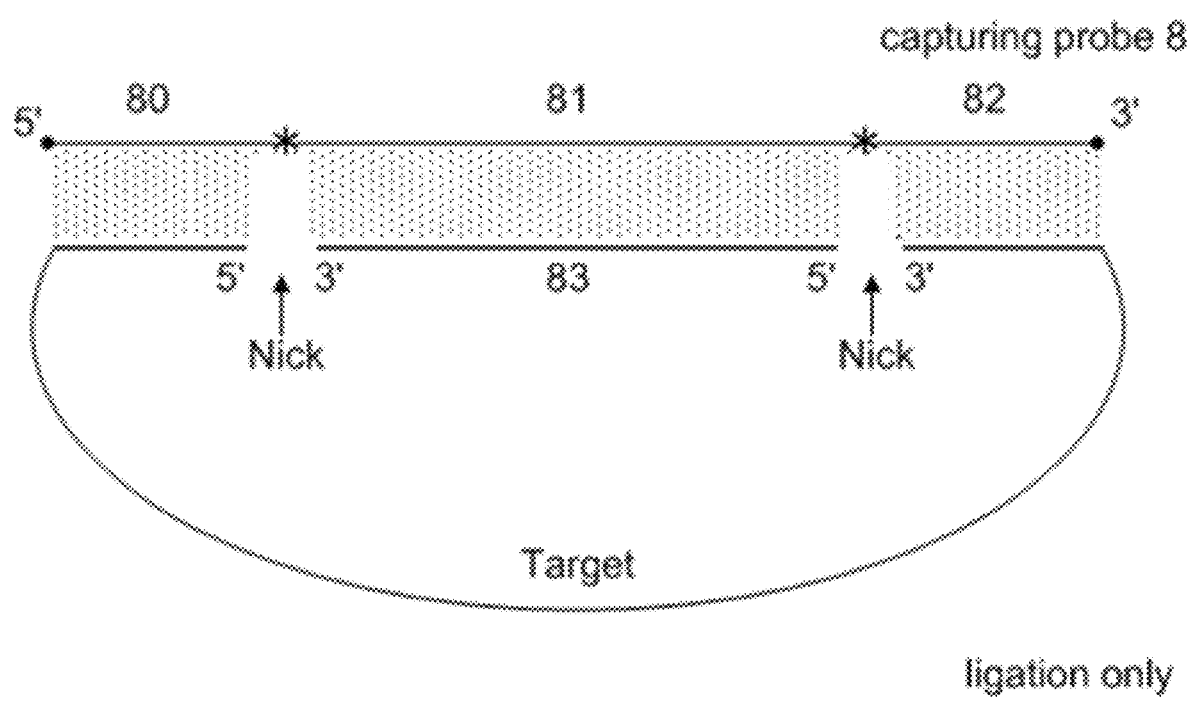

FIG. 7A-C illustrates another aspect of the present disclosure. The 3' end and the 5' end of the target nucleic acid molecule may be formed into a circular probe such that the sequence information of the 3' end and the 5' end is preserved. Subsequent sequencing of the target nucleic acid can elucidate the preserved sequence information of the 3' and/or 5' end.

In one embodiment (FIG. 7A) illustrates the 3' and the 5' end of the target are joined by a single ligation event. In the first step, capturing probe 7 comprising complementary regions 71 and 72 hybridize to the target of interest. If the 3' and the 5' ends of the target perfectly match regions 71 and 72 of the capturing probe, the nick can be joined subsequently by ligation in a second step.

In one embodiment, regions 71 and 72 of capturing probe 7 have a sequence composition and length which support a stable heteroduplex with the target molecule. In another embodiment, only one of regions 71 and 72 have a sequence composition and length which support a stable duplex with the target molecule and the second region has a sequence composition and length which forms a transient or less stable complex.

The sequence length of the stable duplex may be for example, between about 10 nucleotides and about 25 nucleotides. In some embodiments the sequence length of the stable duplex may be about 10 nucleotides, about 20 nucleotides, about 40 nucleotides or longer. The sequence length of the transient or less stable duplex may be for example, between 2 nucleotides and 10 nucleotides. In some embodiments the sequence length of the transient duplex may be 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, or greater than 10 nucleotides greater than 20 nucleotides, greater than 30 nucleotides, greater than 40 nucleotides, or greater than 50 nucleotides.

In another embodiment if the composition or position of only one end of the target is clearly defined, and the composition or position of the other end of the target is unknown, the capturing probe can compose of one region matched to the known sequence and the other region can contain nucleotides which are not base specific (e.g. inosine) to support non-specific formation of duplex.

In order to detect or discriminate the circularized target molecule, after the ligation step, the 3' end of the capturing probe 7 may be extended with a polymerase or amplified by rolling circle amplification and therefore enriched over the background.

In another aspect (FIG. 7B) capturing probe 7 may contain an additional region 73 which forms a gap upon hybridization between the capturing probe and the target molecule. In this case, in a second step following hybridization, two enzymatic reactions are performed. First, the 3' end of the target molecule is extended by a polymerase to close the gap; second, the 3' end of the newly synthesized strand is ligated to the 5' end of the target molecule forming a closed circle. In this case the composition of region 73 may contain additional sequences used for amplification or barcoding. Exonuclease treatment may be used to remove any linear molecules including extension or ligation product or excess capturing probe; the circularized target product can be resistant to exonuclease treatment.

In another aspect (FIG. 7C) capturing probe 8 is partially double stranded. The double stranded region 81 is annealed to another probe 83 such that it forms a stable duplex. Annealing capturing probe 8 in the presence of probe 83 and target molecule, form a heteroduplex molecule with two nicks. If the 5' end and the 3' end of the target molecule perfectly match the probe regions 80 and 82 then ligation of the two nicks can form a hybrid circularized molecule containing the target and probe 83. In this case the composition of region 83 may contain additional sequences used for amplification or barcoding. Exonuclease treatment may be used to remove any linear molecules including extension or ligation product or excess capturing probe; the circularized target product can be resistant to exonuclease treatment.

In some embodiments, the methods of the present disclosure may not comprise sequencing. In some embodiments, a set of loci with specific fragmentation patterns and/or associated with cancer may be identified using any method known in the art. In some embodiments, a set of loci may be identified by array hybridization. In some embodiments, a probe coupled to an array may correspond to an end of a tumor-derived fragment. In some embodiments, a probe coupled to an array may correspond to an end of a non-tumor-derived fragment (e.g., a DNA fragment derived from a normal cell). For example, following enrichment of the biological sample for a set of cell-free DNA fragments, the sample may be contacted to an array comprising one or more oligonucleotide probes corresponding to an end of a tumor-derived fragment. In some instances, sequence information for the tumor-derived fragment ends may be obtained directly from the patient. In some embodiments, sequence information for the tumor-derived fragment ends may be obtained from a database. In some embodiments, identifying a set of loci with specific fragmentation patterns in the plurality of sequence reads may comprise measuring a value of a parameter corresponding to a number of fragments. In some embodiments, identifying a set of loci may comprise measuring a value of a parameter corresponding to a number of tumor-derived DNA fragments. In some embodiments, identifying a set of loci may comprise measuring a value of a parameter corresponding to a number of non-tumor-derived DNA fragments (e.g., DNA fragments derived from normal cells). In some embodiments, identifying a set of loci may comprise measuring a value of a parameter corresponding to a ratio of the number of tumor-derived DNA fragments to a number of non-tumor-derived DNA fragments. In some embodiments, identifying a set of loci may comprise measuring a value of a parameter corresponding to a number of tumor-derived DNA fragments with a particular end sequence. In some embodiments, identifying a set of loci may comprise measuring a value of a parameter corresponding to a ratio of the number of tumor-derived DNA fragments with a particular end sequence to a number of non-tumor-derived DNA fragments. For example, identifying a set of loci with specific fragmentation patterns may comprise measuring a fluorescence signal intensity corresponding to the number of nucleic acid fragments that hybridize to a particular probe on an array.

In all capturing probe designs contained in this disclosure, the capturing probe sequence may contain uracil bases to ensure degradation of excess capturing probe after the enzymatic steps.

Adapter-Mediated Amplification

For the detection of any cancer-associated change in the plasma (or other sample type containing cell-free DNA) of a tested subject, the probability of detecting such a change can theoretically increase with the increase in the number of DNA molecules analyzed. Here we use a hypothetical example to illustrate this principle. Assume that 20% of the plasma DNA in a cancer subject is derived from the tumor, and the tumor has a point mutation at a particular nucleotide position. The mutation occurs only in one of the two homologous chromosomes. As a result, 10% of the plasma DNA covering this particular nucleotide position carry this mutation. If one DNA molecule covering this nucleotide position is analyzed, the probability of detecting the mutation is 10%. If ten plasma DNA molecules covering this nucleotide change are analyzed, the probability of detecting the mutation increases to 65.1% (Probability=$1-0.9^{10}$). If the number of molecules being analyzed is increased to 100, the probability of detecting the mutation increases to 99.99%.

This mathematical principle can be applied to predict the probability of detecting cancer-associated mutations when massively parallel sequencing is used for the analysis of plasma DNA from cancer subjects. However, typical massively parallel sequencing platforms used for sequencing plasma (e.g. the Illumina HiSeq2000 sequencing system with the TruSeq library preparation kit), PCR amplifications can be performed on the template DNA before sequencing.

Amplification can refer to processes that result in increases (more than 1-fold) in the amount of template DNA when compared with the original input nucleic acid. However, current methods of amplification can fail to preserve the sequence information at the ends of template nucleic acid fragments. In some embodiments, amplification processes can be performed before the DNA template analysis step, e.g. sequencing, to amplify nucleic acids in samples having low total cell-free DNA concentration or a low concentration of nucleic acids of interest (e.g., tumor-derived DNA). In some cases, amplification can be performed using adapters attached to ends of nucleic acid fragments, wherein the adapters are capable of being separated from the nucleic acid fragment following amplification. Furthermore, in some cases, the separation of the adapter from the nucleic acid fragment results in minimal or no loss of sequence information (e.g., nucleotides) from the nucleic acid fragment (e.g., the separation occurs at a junction between the nucleic acid fragment and the adapter).

Sequencing may be performed in some embodiments of the present disclosure. For example, sequencing of genomic DNA or tumor-derived nucleic acids may be performed to determine a set of loci corresponding to fragmentation sites of tumor-derived nucleic acids. Sequencing a nucleic acid can be performed using any method known in the art. In some embodiments, sequencing can include next generation sequencing (e.g., Illumina/Solexa sequencing, Roche 454 sequencing, Ion torrent sequencing, and/or SOLiD sequencing.

Roche 454 sequencing can generally refer to a pyrosequencing technology which utilizes the use of the enzymes ATP sulfurylase and luciferase. After the incorporation of each nucleotide by DNA polymerase, a pyrophosphate can be released, which further takes part in downstream light-producing reactions. The amount of light can be proportional to the incorporated number of nucleotides. The DNA can be fragmented and adapters can be ligated at both ends. The fragments can be mixed with agarose beads, which carry adapters complementary to the library adapters, and thus each bead can be associated with a unique DNA fragment. The beads and DNA fragments can be isolated in individual micelles, where emulsion PCR takes place and million copies of the single fragments can be amplified onto the surface of each bead. Each bead can be placed in a well of picotiter plate (PTP), as the wells have dimensions such that only one bead can fit per well. Enzymes can be added to the beads and pure nucleotide solutions can be added with an immediate imaging step. On one side of the array a CCD (charge-optic device) camera records the light emitted from each bead. The first four nucleotides (TCGA) can be the same as the start of the adapter, which allows for the emitted light to be calibrated according to the type of nucleotide added.

Illumina sequencing can comprise three steps: amplification, sequencing, and analysis. Nucleic acids can be chopped up into smaller pieces and given adapters, indices, and other kinds of molecular modifications that act as reference points during amplification, sequencing, and analysis. The modified nucleic acid can be loaded onto a specialized chip where amplification and sequencing will take place. Along the bottom of the chip can be hundreds of thousands of oligonucleotides (short, synthetic pieces of nucleic acid). They can be anchored to the chip and able to grab nucleic acid fragments that have complementary sequences. Once the fragments have attached, a phase called cluster generation begins. This step makes about a thousand copies of each fragment of nucleic acid. Next, primers and modified nucleotides enter the chip. These nucleotides have reversible 3' blockers that force the primers to add on only one nucleotide at a time as well as fluorescent tags. After each round of synthesis, a camera takes a picture of the chip. A computer determines what base was added by the wavelength of the fluorescent tag and records it for every spot on the chip. After each round, non-incorporated molecules can be washed away. A chemical deblocking step can then be used in the removal of the 3' terminal blocking group and the dye in a single step. The process continues until the full nucleic acid molecule can be sequenced. With this technology, thousands of places throughout the genome can be sequenced at once via massive parallel sequencing.

Ion semiconductor sequencing can refer to a method of DNA sequencing based on the detection of hydrogen ions that can be released during the polymerization of DNA. This can be a method of "sequencing by synthesis", during which a complementary strand can be built based on the sequence of a template strand. A microwell containing a template DNA strand to be sequenced can be flooded with a single species of deoxyribonucleotide triphosphate (dNTP). If the introduced dNTP can be complementary to the leading template nucleotide, it can be incorporated into the growing complementary strand. This causes the release of a hydrogen ion that triggers an ISFET ion sensor, which indicates that a reaction has occurred. If homopolymer repeats can be present in the template sequence, multiple dNTP molecules will be incorporated in a single cycle. This leads to a corresponding number of released hydrogens and a proportionally higher electronic signal.

SOLiD sequencing can generally refer to a platform that utilizes a DNA fragment library, which can be flanked by ligated adapters. The fragments can be attached to small paramagnetic beads and emulsion PCR can be performed to amplify the fragments. Sequencing by synthesis can be performed by utilizing DNA ligase, rather than polymerase. Each cycle of sequencing involves the ligation of a degenerate population of fluorescently labeled universal octamer primers. A specific position of the octamer (e.g., base 5) carries a fluorescent label. After ligation, images can be acquired in four channels, followed by cleavage of the octamer between positions 5 and 6, removing the fluorescent label. After several rounds of octamer ligation, which enable sequencing of every 5th base (e.g., bases 5, 10, 15, and 20), the extended primer can be denatured. Different primers can be used to examine the previous or next positions (e.g., base 3 or 6).

In some embodiments, sequencing the nucleic acid can be performed using chain termination sequencing, hybridization sequencing, mass spectrophotometry sequencing, massively parallel signature sequencing (MPSS), Maxam-Gilbert sequencing, nanopore sequencing, polony sequencing, pyrosequencing, shotgun sequencing, single molecule real time (SMRT) sequencing, or any combination thereof.

The number or the average number of times that a particular nucleotide within the nucleic acid can be read during the sequencing process (e.g., the sequencing depth) can be multiple times larger than the length of the nucleic acid being sequenced. In some instances, when the sequencing depth is sufficiently larger (e.g., by at least a factor of 5) than the length of the nucleic acid, the sequencing can be referred to as 'deep sequencing'. In any of the embodiments disclosed herein, analyzing the nucleic acid can comprise deep sequencing. For example, a nucleic acid can be sequenced such that the sequencing depth is about 20 times greater than the length of the nucleic acid. In some instances, when the sequencing depth is at least about 100 times greater than the length of the nucleic acid, the sequencing can be referred to as 'ultra-deep sequencing'. In any of the embodiments disclosed herein, analyzing the nucleic acid can comprise ultra-deep sequencing. In some embodiments, the sequencing depth can be one average at least about 5 times greater, at least about 10 times greater, at least about 20 times greater, at least about 30 times greater, at least about 40 times greater, at least about 50 times greater, at least about 60 times greater, at least about 70 times greater, at least about 80 times greater, at least about 90 times.

FIGS. 8A-B illustrate an embodiment of the present disclosure wherein adapters (1 and 2) are ligated to each blunt end of a nucleic acid fragment, and primers are bound to the adapters to amplify the nucleic acid fragment. In some cases, nucleic acid fragmentation can yield nucleic acid fragments having damaged ends. Non-limiting examples of a damaged nucleic acid end can include an end having a 3' overhang, a 5' overhang, and a 3' or 5' end comprising a partial or damaged nucleotide. These damaged ends can reduce the efficiency of ligation of adapters, or prevent the ability of adapter to ligate to the nucleic acid entirely. Accordingly, in some aspects of the present disclosure, damaged nucleic acids may be blunted to create an end that is capable of being ligated to an adapter (FIG. 8A). Once ligated, primers may be used to bind to the adapters for subsequent amplification of the nucleic acid fragments (FIG. 8B).

By incorporating a recognition sequence for a nuclease having a cleavage site outside of the recognition sequence (e.g., a cleavage site occurring at the junction of the nucleic acid fragment and the adapter), the adapter can be separated from the nucleic acid sequence following amplification while preserving the sequence information at one or more ends of the nucleic acid fragment. A person having skill in the art will appreciate that amplification of a nucleic acid can be performed by a variety of techniques. Non-limiting examples of amplification techniques include reverse transcription-PCR, real-time PCR, quantitative real-time PCR, digital PCR (dPCR), digital emulsion PCR (dePCR), clonal PCR, amplified fragment length polymorphism PCR (AFLP PCR), allele specific PCR, assembly PCR, asymmetric PCR (in which a great excess of primers for a chosen strand can be used), colony PCR, helicase-dependent amplification (HDA), Hot Start PCR, inverse PCR (IPCR), in situ PCR, long PCR (extension of DNA greater than about 5 kilobases), multiplex PCR, nested PCR (uses more than one pair of primers), single-cell PCR, touchdown PCR, loop-mediated isothermal PCR (LAMP), recombinase polymerase amplification (RPA), and nucleic acid sequence based amplification (NASBA). In some cases, amplification comprises linear amplification, isothermal amplification, or isothermal linear amplification. One technique for nucleic acid amplification is PCR. In general, PCR is a process of nucleic acid amplification that involves an enzymatic chain reaction for preparing exponential quantities of a specific nucleic acid sequence. Specifically, PCR can involve cycling the temperature of the reaction to denature nucleic acids into single strands, anneal primers to regions of the nucleic acid that are complementary to the primers, and copy the denatured nucleic acid by extension or elongation from the primer using an enzyme and nucleotides. This process can result in newly synthesized extension products. These newly synthesized sequences can become templates for the primers, and repeated cycles of denaturing, primer annealing, and extension can result in exponential accumulation of the specific sequence being amplified.

In some embodiments, the amplifying can be performed at a single temperature. For example, amplifying the nucleic acid can comprise PCR, and the PCR can be performed at 72 degrees Celsius. In some embodiments, the amplifying can be performed at about 20 degrees Celsius, about 25 degrees Celsius, about 30 degrees Celsius, about 35 degrees Celsius, about 40 degrees Celsius, about 45 degrees Celsius, about 50 degrees Celsius, about 55 degrees Celsius, about 60 degrees Celsius, about 65 degrees Celsius, about 70 degrees Celsius, about 75 degrees Celsius, about 80 degrees Celsius, about 85 degrees Celsius, about 90 degrees Celsius, about 95 degrees Celsius, about 100 degrees Celsius, or greater than about 100 degrees Celsius. In some embodiments, the amplifying can be performed at multiple temperatures. For example, the amplifying can comprise performing PCR, and the PCR reaction can comprise a first step (e.g., denaturation) at a first temperature, a second step (e.g., annealing) at a second temperature, and a third step (e.g., extension or elongation) at a third temperature. A person having skill in the art will appreciate that the PCR reaction can comprise any number of steps, each step being performed at a given temperature. In some embodiments, at least two steps can be performed at the same temperature. In some embodiments, at least two steps can be performed at different temperatures. For example, the amplifying can comprise performing PCR, and the PCR reaction can comprise a denaturation step at about 95 degrees Celsius, an annealing step at about 55 degrees Celsius, and an extension step at about 75 degrees Celsius. In some embodiments, the amplifying can comprise multiple cycles of multiple temperatures. In some embodiments, the amplifying can comprise at least 5 cycles. In some embodiments, the amplifying can comprise about 10, about 15, about 20, about 25, about 30, about 35, about 40, about 45, or about 50 cycles. In some embodiments, the amplifying can comprise greater than about 50 cycles. In some embodiments, each cycle can comprise any number of steps, performed at any number of different temperatures. For example, the amplifying can comprise performing PCR, and the PCR reaction can comprise performing 25 cycles, wherein one cycle constitutes performing a denaturation step followed by an annealing step followed by an extension step. In some embodiments, the amplifying can comprise multiple cycles, each cycle can comprise multiple steps, and each step within a given cycle can occur over any amount of time. For example, the amplifying can comprise performing PCR, and the PCR reaction can comprise performing 30 cycles, wherein one cycle constitutes performing a denaturation step for 2 minutes followed by an annealing step for 1 minute followed by an extension step for 1 minute. Any step within a cycle can be performed for any amount of time. In some embodiments, a step can be performed for at most about 5 seconds. In some embodiments, a step can be performed for at least about 5 second, at least about 10 seconds, at least about 20 seconds, at least about 30 seconds, at least about 45 seconds, at least about 60 seconds, at least about 90 seconds, at least about 120 seconds, at least about 150 seconds, at least about 180 seconds, at least about 210 seconds, at least about 240 seconds, at least about 270 seconds, or at least about 300 seconds. In some embodiments, a step can be performed for greater than about 300 seconds.

Figure 9A:
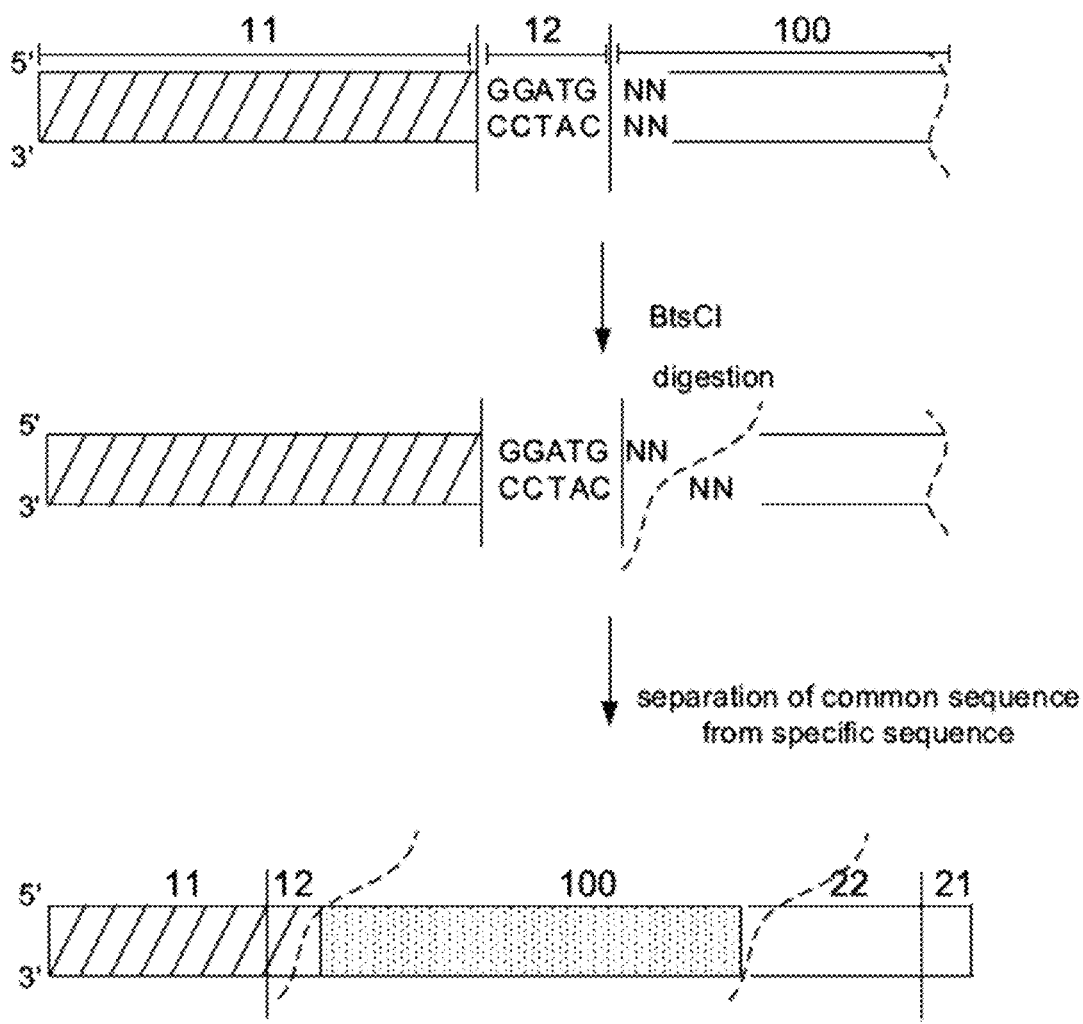
FIGS. 9 A-B illustrate separation of the adapter from the nucleic acid fragment at a Type Hs cleavage site, wherein the adapter comprises a Type Hs enzyme recognition sequence and the enzyme cleavage site is located at the end of the nucleic acid fragment.
FIG. 9B discloses SEQ ID NOS 3-4, 3 and 5, respectively, in order of appearance.
Figure 9B:
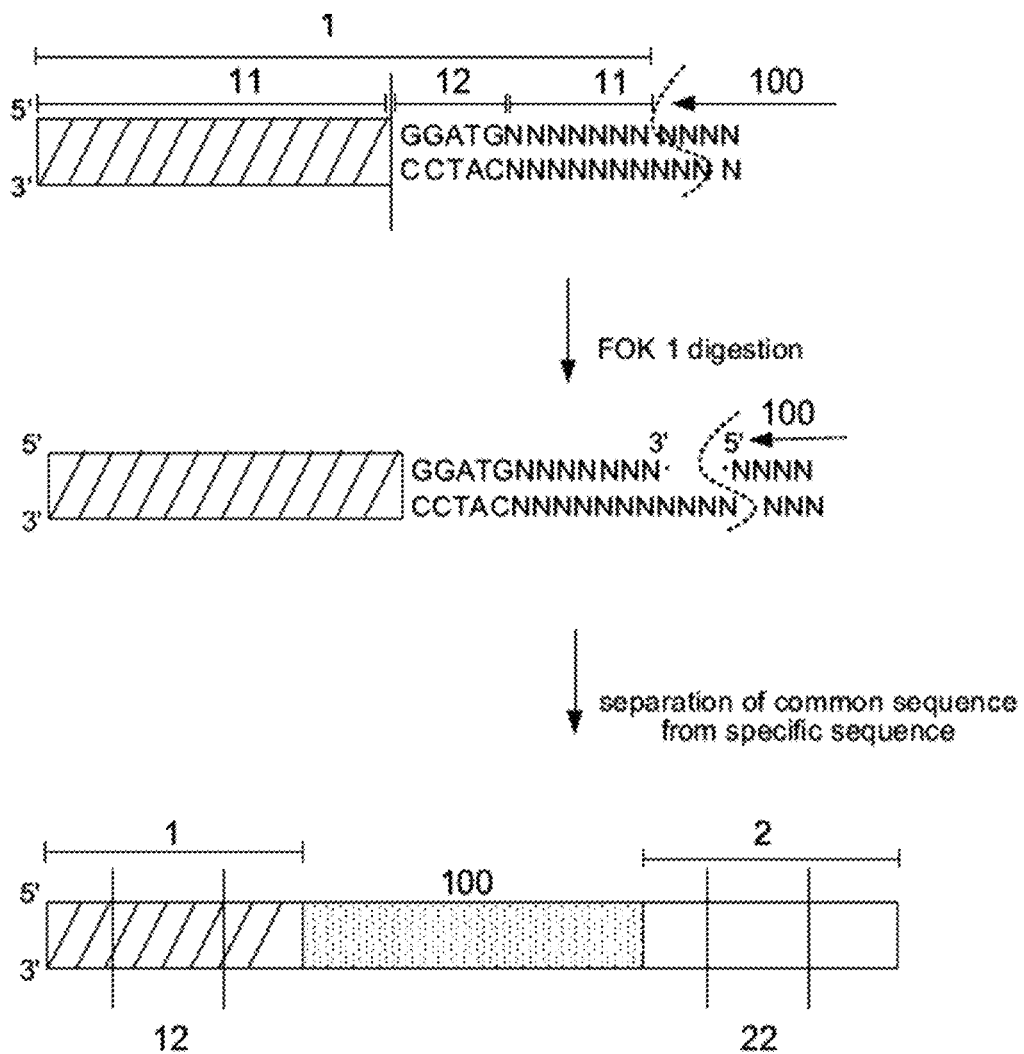

As shown in FIGS. 9A-B, an adapter (11+12) comprising a nuclease recognition sequence (12) for a nuclease that cleaves outside of the nuclease recognition site is ligated to a nucleic acid fragment (100). In particular, the cleavage site (dashed line) occurs at a junction between the adapter and the nucleic acid fragment. The nuclease recognition site may be separated from the junction between the adapter and the nucleic acid fragment by any number of nucleotides. Following amplification of the nucleic acid fragment, the adapters may be removed by cleaving the adapter from the nucleic acid fragment at the cleavage site. The adapter may be any number of nucleotides in length. In some embodiments, the adapter can comprise about 3 nucleotides, about 4 nucleotides, about 5 nucleotides, about 6 nucleotides, about 7 nucleotides, about 8 nucleotides, about 9 nucleotides, about 10 nucleotides, about 15 nucleotides, about 20 nucleotides, about 25 nucleotides, about 30 nucleotides, about 35 nucleotides, about 40 nucleotides, about 45 nucleotides, about 50 nucleotides, or greater than about 50 nucleotides. The adapter can comprise a recognition site (e.g., a recognition sequence) for a nuclease having a cleavage site at a junction between the adapter and the nucleic acid fragment. The recognition sequence may be any sequence capable of being recognized and/or bound by a nuclease. In some embodiments, the nuclease may be a Type IIs nuclease. Non limiting examples of Type IIs nucleases include AcuI, AlwI, BaeI, BbsI*, BbsI-HF*, BbvI, BccI, BceAI, BcgI, BciVI, BcoDI, BfuAI, BmrI, BpmI, BpuEI, BsaI*, BsaI-HF®, BsaXI, BseRI, BsgI, BsmAI, BsmBI*, BsmFI, BsmI, BspCNI, BspMI, BspQI, BsrDI, BsrI, BtgZI*, BtsCI, BtsI, BtsIMutI, CspCI, EarI, FauI, FokI, HgaI, HphI, HpyAV, MboII, MlyI, MmeI, MnlI, NmeAIII, PleI, SapI*, and SfaNI. In some embodiments, the recognition sequence may be at an end of the adapter that binds to the nucleic acid fragment (e.g., adjacent to a junction between the adapter and the nucleic acid fragment). In some embodiments, the nuclease recognition sequence may be separated from the junction between the adapter and the nucleic acid fragment by about 1 nucleotide, about 2 nucleotides, about 3 nucleotides, about 4 nucleotides, about 5 nucleotides, about 6 nucleotides, about 7 nucleotides, about 8 nucleotides, about 9 nucleotides, about 10 nucleotides, about 15 nucleotides, about 20 nucleotides, about 25 nucleotides, about 30 nucleotides, about 35 nucleotides, about 40 nucleotides, about 45 nucleotides, about 50 nucleotides, or greater than about 50 nucleotides.

Figure 10A:
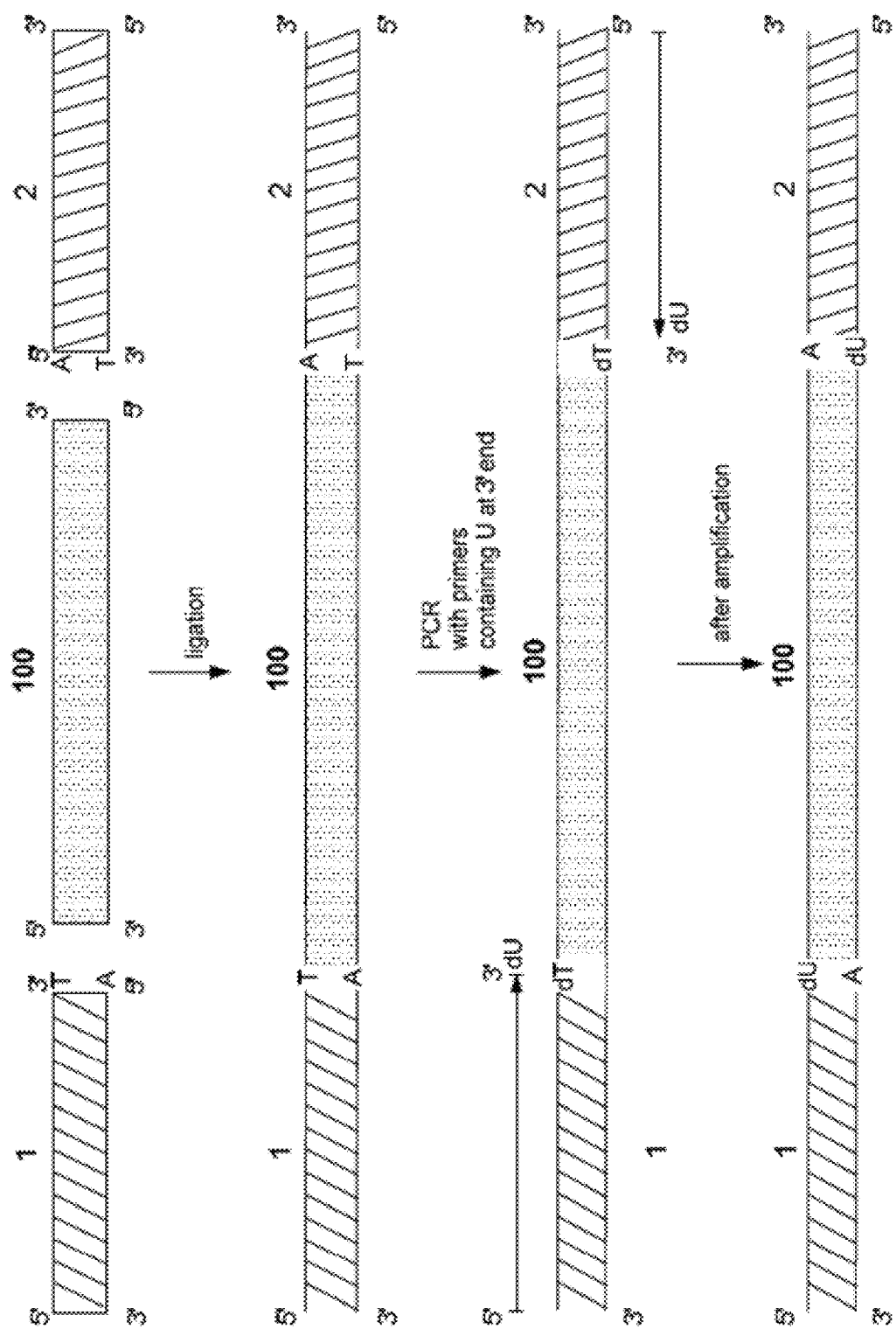
FIGS. 10 A-C illustrate an embodiment of the present disclosure wherein adapters comprising thymine (T) and/or thymidine bases at an end of the adapter are ligated to a nucleic acid fragment, dU is introduced into an amplification product, an AP site is generated, and the site is cleaved.
Figure 10B:
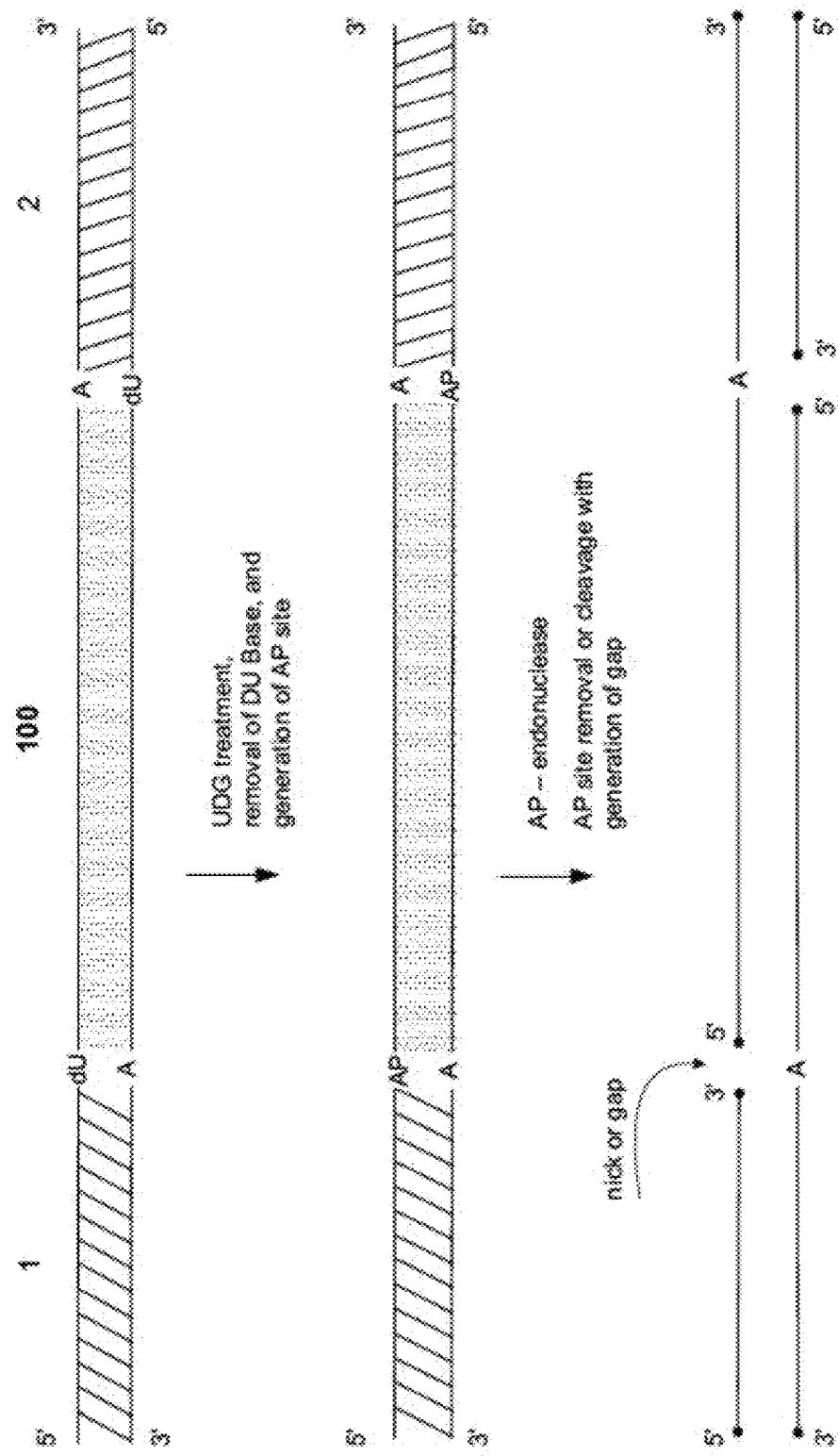

FIGS. 10 A-C illustrate another embodiment of the present disclosure wherein adapters (1 and 2) comprising Thymine (T) and/or Thymidine bases at an end of the adapter are ligated to a nucleic acid fragment (100). PCR is subsequently performed to amplify the nucleic acid fragment and substitute the Thymine (T) and/or Thymidine bases with Uracil, Uridine, and/or Deoxyuridine bases between the adapters and the ends of the nucleic acid fragment (FIG. 10A, bottom). Having substituted Thymine (T) and/or Thymidine bases with Uracil, Uridine, and/or Deoxyuridine bases, Uracil-DNA Glycosylase (UDG) treatment may be performed to substitute the Uracil, Uridine, and/or Deoxyuridine bases with an Apurinic/Apyrimidinic (AP) site in an amplicon (e.g., a product of the amplification of a nucleic acid). The method can comprise subsequent treatment with an AP endonuclease to generate a nick at the AP site (FIG. 10B, bottom), and treatment with a nuclease specific for single stranded nucleic acids to separate the adapter from the nucleic acid fragment (FIG. 10C, bottom). Various agents may be used to cleave the phosphodiester backbone of a polynucleotide at an AP site. In some cases, the agent is an AP endonuclease. In other embodiments, the agent is N,N'-dimethylethylenediamine (DMED). In other embodiments, the agent can be heat, basic conditions, acidic conditions, or an alkylating agent. It is contemplated that additional Uracil, Uridine, and/or Deoxyuridine bases may be incorporated into one or more other positions in the adapter (e.g., other than the end of the adapter) which can improve the efficiency of degradation of the adapter. It is also contemplated that other types of modified bases may be used (e.g., instead of dU). For example RNA bases can be incorporated into primer sequences that bind to the adapter, and then cleaved with RNAse enzyme; 8-oxoguanine or other modified bases can be cleaved by DNA repair enzymes (e.g., Fpg).

FIG. 11 illustrates another embodiment of the present disclosure wherein, following treatment with an AP endonuclease to generate a nick at an AP site, heat is used to denature and remove a single stranded portion of the adapter. Subsequent treatment with a nuclease specific for single stranded nucleic acids is used to separate the remaining single stranded portion of the adapter from the nucleic acid fragment. Incorporation of additional Uracil, Uridine, and/or Deoxyuridine bases into one or more other positions in the adapter (e.g., other than the end of the adapter) can improve the efficiency of degradation of the adapter when using heat to denature the adapters.

EXAMPLES

The following examples are included for illustrative purposes only and are not intended to limit the scope of the invention.

Example 1. Capturing Liver Specific DNA Fragments in Plasma by Gapfill Chemistry From genotyping data of a liver-transplant recipient, donor-specific single nucleotide polymorphism (SNPs) are identified. From the sequencing data, fragments that overlap with donor-specific SNPs are selected. The top sites that contain donor-specific SNPs are used to design capturing probes and synthetic targets. Within each top site, donor specific fragments that (a) have common 5' ends, and/or (b) are distinguishable from non-donor-specific fragments, are chosen for oligo design.

Synthetic Targets

Each donor-specific target has at least two sequences of different length. Both sequences have the same 5' end but different 3' ends, representing the short and long fragments of a population. For example:

```
Short:
                                    (SEQ ID NO: 1)
ACAATACCTGGCGGTGTGTCTGTGAGGTCTGAATAAAAATTAAATGC

GCAAAGGCAGGTAAGATCCTGAGCTCAGTGCCCGGTGCACAGACACC

ATTGCGGGTGTGGTTCCTGTCATTACTCAGGGCCTGCCCTGGTGTGT

ATGT

Long:
                                    (SEQ ID NO: 2)
ACAATACCTGGCGGTGTGTCTGTGAGGTCTGAATAAAAATTAAATGC

GCAAAGGCAGGTAAGATCCTGAGCTCAGTGCCCGGTGCACAGACACC

ATTGCGGGTGTGGTTCCTGTCATTACTCAGGGCCTGCCCTGGTGTGT

ATGTGACTGCATGTGTTTGTGT
```

Ultramer® oligo nucleotides of both sequences can be ordered as synthetic targets, e.g., from Integrated DNA Technologies (IDT®).

Capturing/Gapfill Probes

Figure 12A:
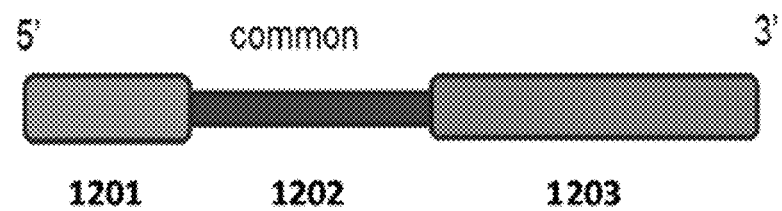
FIG. 12A illustrates an exemplary capture probe comprising a 5' end, a common sequence, and a 3' end.
Figure 12B:
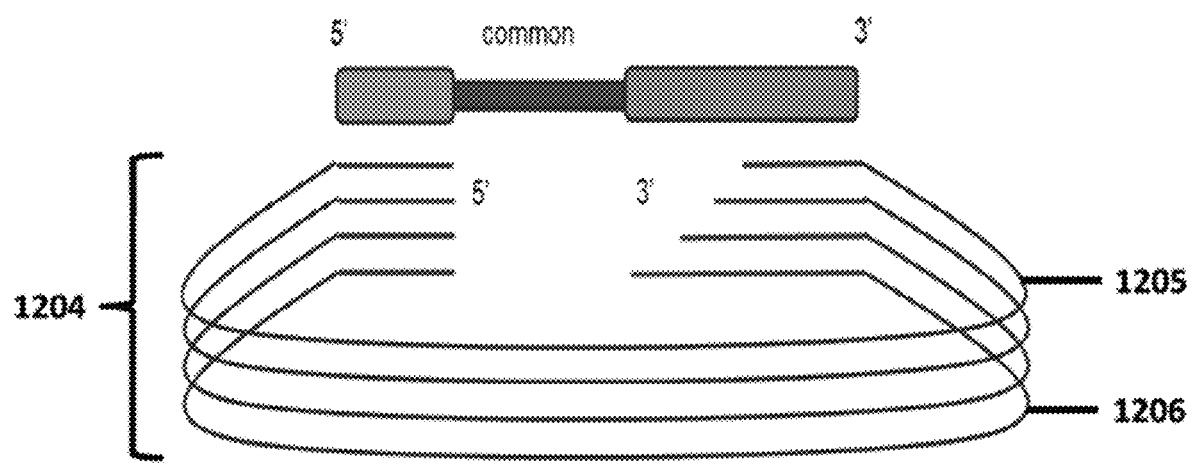
FIG. 12B illustrates a capture probe and 4 potential hybridization targets of varying lengths.

The probes are also designed based on the aforementioned two sequences. A capturing probe can have three segments. An exemplary probe is show in in FIG. 12A. The 5' end (1201) of the probe is complementary to common 5' end of the target (e.g., about 20 bases). The common sequence (1202) contains target sequences for a qPCR probe. The 3' end (1203) of the probe is complementary to 3' ends of the target (1204 depicts multiple targets). It contains (a) sequences that are complementary to ~20 bases of the 3' end of the short target, and (b) additional sequences that complementary to 3' end of the long target. As shown in FIG. 12B, the probe will capture short (1205) and long (1206) targets and sequences in between the two different 3' ends. The capture probe is capable of capturing (e.g., hybridizing) with a target nucleic acid of any length.

Kits are also contemplated. For example, a kit can comprise one or more capture probes, and one or more reagents for performing a method of the present disclosure (e.g., reagents for amplifying a target nucleic acid). In another example, a kit can comprise one or more capture probes, and instructions for directing a subject to use the nucleic acid probe set to analyze the cell-free nucleic acid molecules in the biological sample from the subject qPCR Primers qPCR primers are designed from the sequences flanking the 5' and 3' ends of the targets. The directions of the PCR are facing away from each other so there would not PCR signal unless the capturing and gapfill steps can close the gap.

Capturing and Gapfill Workflow

Figure 13:
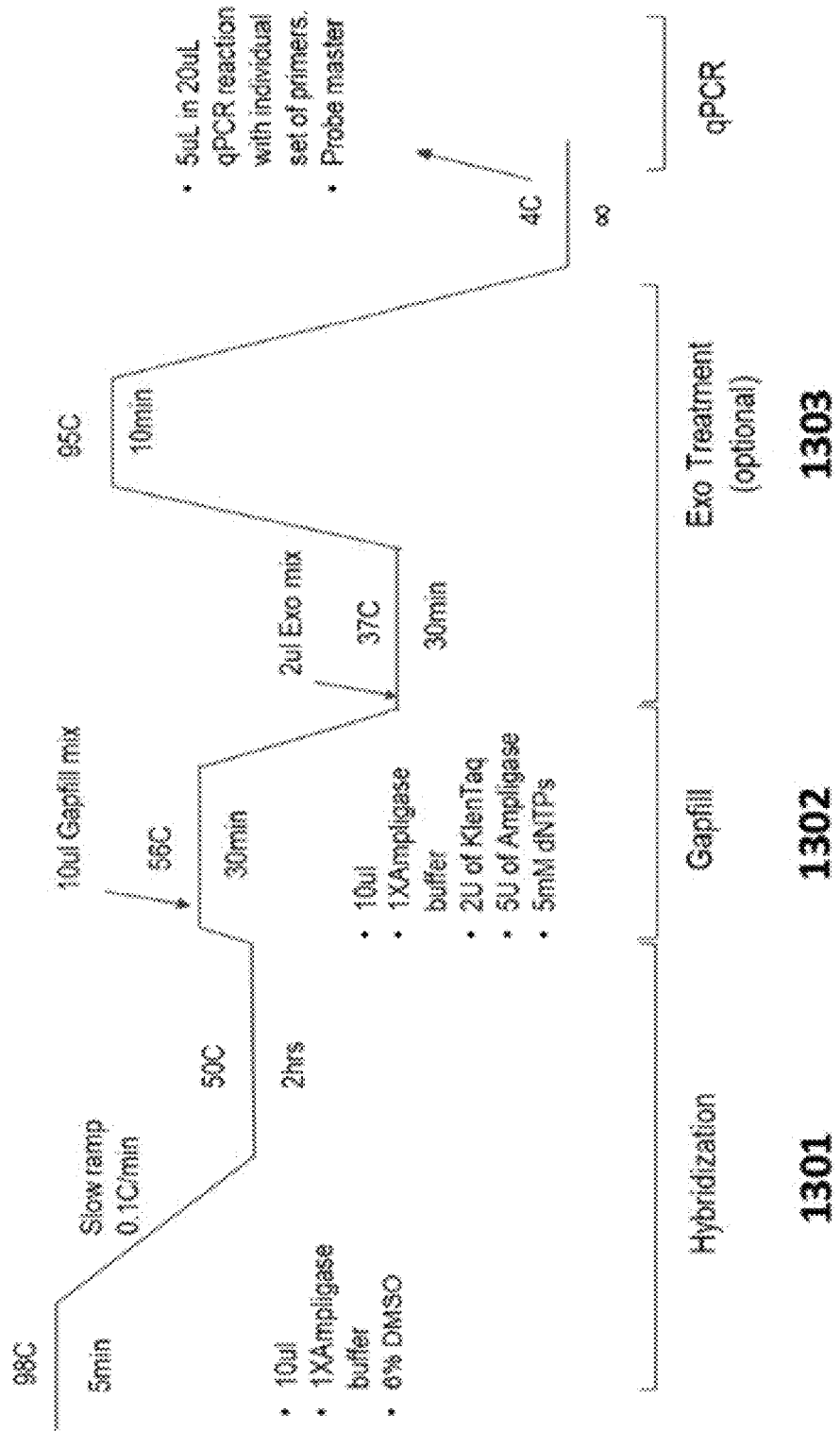
FIG. 13 illustrates an exemplary thermocycling workflow according to methods of the present disclosure.

The workflow can generally consist of 3 steps (e.g., Hybridization, Gapfill and an optional Exo Treatment step), followed by qPCR. An exemplary thermocycling protocol is shown in FIG. 13. The workflow starts with the Hybridization step (1301); individual or pool of the synthetic targets are mixed with individual probes in 10 uL of 1× Ampligase buffer and additive such as DMSO. The amount of probe per reaction is 1 nmole and the amount of target per reaction varies from 100 amoles to 10 zmoles. The mixture is heated to 98 C for 5 minutes, slowly cooled to 50 C and incubated for 2 hours.

Figure 14A:
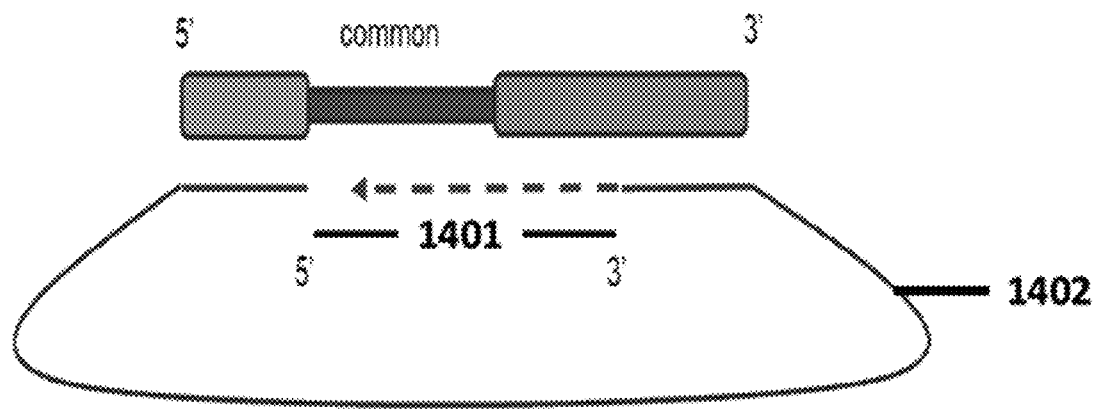
FIG. 14A illustrates a capture probe hybridized to a target nucleic acid, and a gapfill reaction being performed to synthesize a sequence between the 3' and 5' ends of the target nucleic acid.
Figure 14B:
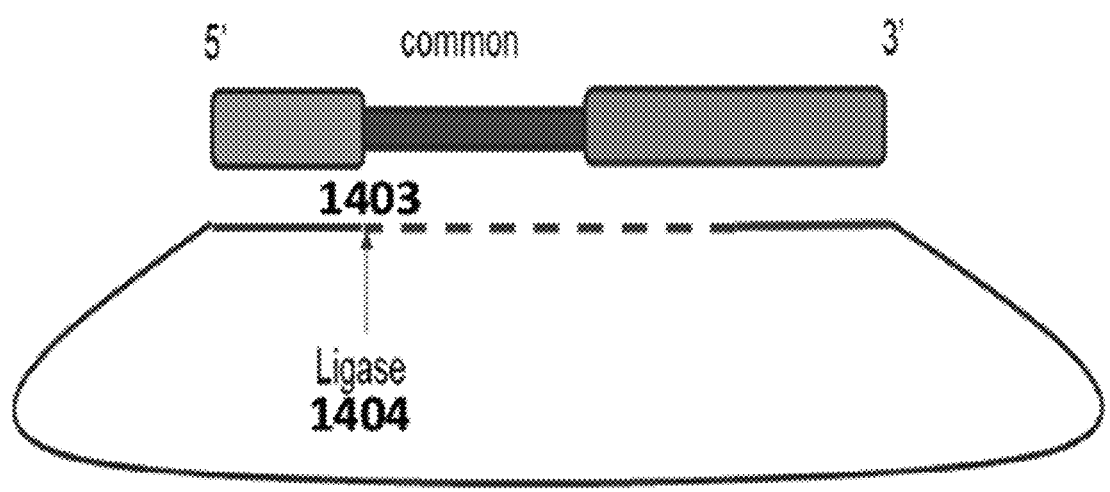
FIG. 14B illustrates ligating the 3' and 5' ends of the target nucleic acid using a ligase following a gapfill reaction, thereby circularizing the target nucleic acid.

Next, during the Gapfill step (1302), the reaction mixture is then heated to 56 C. 10 ul of the Gapfill mix is added. The Gapfill mix contains 1× Ampligase buffer, 2 U of KlenTaq (lacks exonuclease activities), 5 U of Amligase, and 10 uM dNTPs. The reaction is incubated at 56 C for 30 minutes. As shown in FIG. 14A, a gapfill reaction is shown where the gap (1401) is filled by polymerase and dNTP which copies the common portion (e.g., qPCR probe) to the target (1402) molecule. As shown in FIG. 14B, the nick (1403) is sealed by ligase (1404) and the target molecule is circularized.

Figure 15:
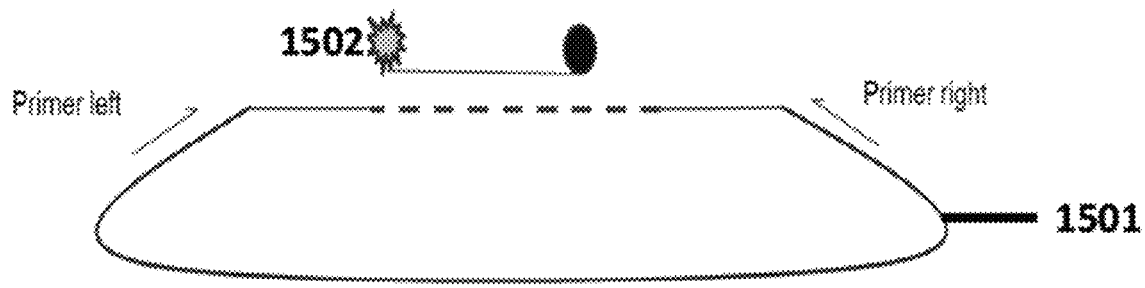
FIG. 15 illustrates qPCR being performed on a circularized target nucleic acid.

The Exo treatment is optional (1303), to remove probes and non-circularized targets. 2 uL of Exo I (20 U) and Exo III (200 U) is added after the temperature is lower to 37 C. The incubation is 30 minutes and exonucleases are deactivated at 95 C for 10 minutes. The resulting circularized target (1501) can be detected in qPCR, as shown in FIG. 15. Real Time quantitative PCR (qPCR) is very similar to traditional PCR. The major difference being that with qPCR the amount of PCR product is measured after each round of amplification while with traditional PCR, the amount of PCR product is measured only at the end point of amplification. Amplification products are measured as they are produced using a fluorescent label (1502). During amplification, a fluorescent dye binds, either directly or indirectly via a labeled hybridizing probe (1503), to the accumulating nucleic acid molecules, and fluorescence values are recorded during each cycle of the amplification process. The fluorescence signal is directly proportional to nucleic acid concentration over a broad range, and the linear correlation between PCR product and fluorescence intensity is used to calculate the amount of template present at the beginning of the reaction. The point at which fluorescence is first detected as statistically significant above the baseline or background is called the threshold cycle or Ct Value. This threshold can be established to quantify the amount of nucleic acid in the samples. It can be inversely correlated to the logarithm of the initial copy number. The threshold can be set above the amplification baseline and within the exponential increase phase (which looks linear in the log phase). Instruments can automatically calculate the threshold level of fluorescence signal by determining the baseline (background) average signal and setting a threshold 10-fold higher than this average. In theory, an equal number of molecules are present in all of the reactions at any given fluorescence level. Therefore, at the threshold level, it is assumed that all reactions contain an equal number of specific amplicons. The higher the initial amount of sample nucleic acid, the sooner the accumulated product is detected in the fluorescence plot, and the lower the Ct value.

Sample Results

Figure 16:
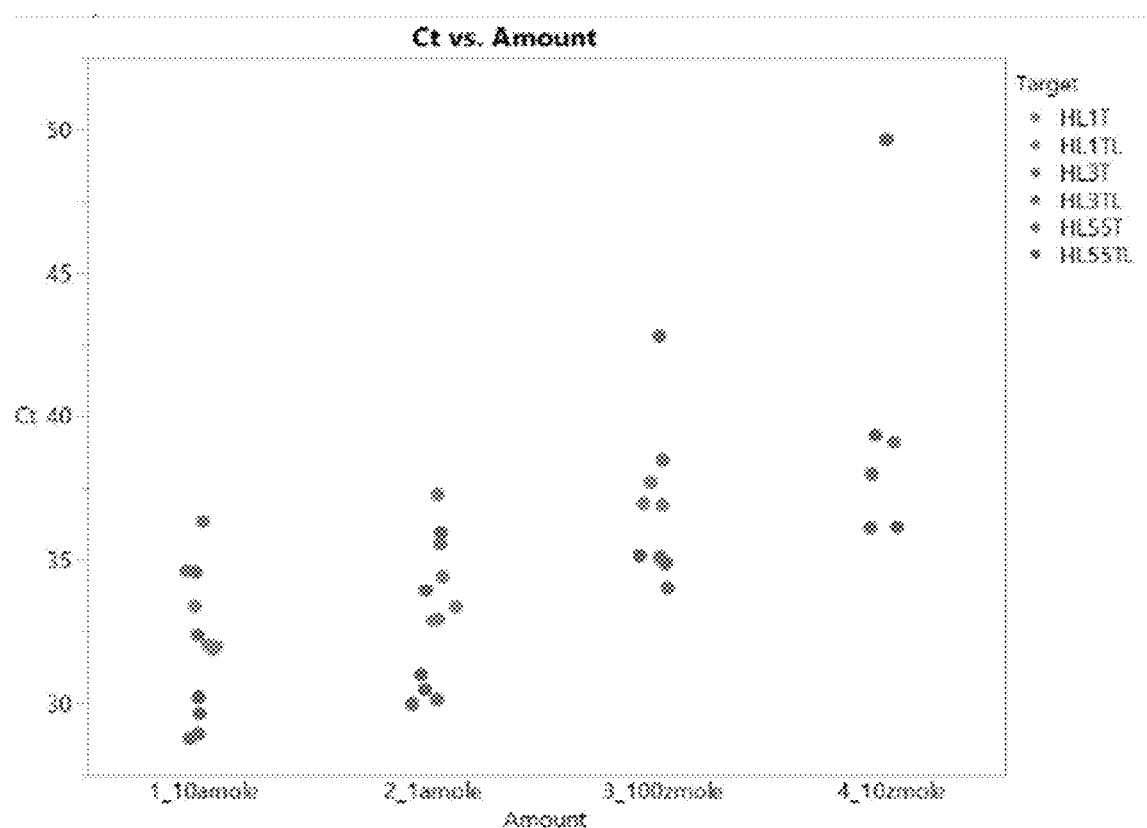
FIG. 16 depicts exemplary results showing a correlation between a concentration of a target nucleic acid and a qPCR signal.

Putative liver-specific targets are tested individually in a titration experiment. The amount of targets per reaction are 10 amoles, 1 amole, 100 zmoles and 10 zmoles. Human genomic DNA is used as carrier. Exemplary results are shown in FIG. 16. Four points (1 thru 4) in the dilution series of target to show that the signal is specific and sensitive. Point 1 is 1_10 amole (e.g., 10 attomole of target in a 20 ul reaction), Point 2 is 2_1 amole (e.g., 1 attomole of target in a 20 ul reaction), Point 3 is 3_100 zmole (e.g., 100 zeptomole of target in a 20 ul reaction), and Point 4_10 zmole is 10 zeptomole of target in the 20 ul reaction). In the legend, HL corresponds to human liver. The target represents liver-specific fragment ends in plasma, based on previous NGS studies. The 'T' in target nomenclarure corresponds to 'Target' and the 'TL' corresponds to 'Long Target', since two sizes of target were analyzed in this experiment. As the amount of the target increases, the qPCR signal increases (e.g., decreasing Ct values). Both short (e.g. HL55TL) and long (e.g. HL55T) targets are detectable and show similar dose response.

Example 2. Target-Specific Enrichment of Tumor-Derived Nucleic Acids for Cancer Screening Target-specific enrichment may be used to increase the concentration of target nucleic acids of interest. Amplification of specific nucleic acids of interest (e.g., cell-free nucleic acids, tumor-derived nucleic acids, or nucleic acid fragments aligning to specific chromosomal locations) using target-specific capture probes can reduce the sequencing depth and/or breadth to achieve clinical sensitivity or specificity for a diagnostic test.

In one example, a blood sample obtained from a human patient is centrifuged to separate plasma from remaining blood components (e.g., red blood cells, white blood cells and platelets). Cells are removed from plasma by centrifugation for 10 minutes at 1,000-2,000×g using a refrigerated centrifuge. Centrifugation for 15 minutes at 2,000×g depletes platelets in the plasma sample. Following centrifugation, the plasma sample is immediately transferred into a clean polypropylene tube using a Pasteur pipette. The sample is maintained at 2-8° C. while handling.

To enrich the sample for tumor-derived nucleic acids, a set of single-stranded capture probes is designed that hybridize to unique target nucleic acid sequences (e.g., corresponding to different regions of the human genome). Each capture probe is approximately 40 bases in length and includes (i) a target nucleic binding region and (ii) a region that does not bind to the target nucleic acid and has a sequence complementary to a ligation probe. A reaction mixture is prepared with a the set of capture probes (10 micromolar) and ligation probes (5 micromolar) in 100 mM potassium phosphate buffer pH 7, and added to 10 ng DNA extract from the plasma sample (20 μl total reaction volume). Following hybridization of the capture probes to the target nucleic acid, and subsequent hybridization of the ligation probes to the capture probes, the ligation probe is ligated to the target nucleic acid. 2 μl of T4 DNA ligase is added to the mixture; the mixture is incubated at room temperature for approximately 10 minutes, and heat inactivated at 65° C. for 10 minutes. The ligation probes comprise primer sequence for subsequent amplification and barcode sequence. PCR amplification is carried out using Go Taq® Green Master Mix. Each PCR reaction mixture consists of 20 μl PCR master mix; 4 μM of each of the forward and reverse primers, and added to the reaction mixture. Thermal cycling starts by a first denaturation step of 4 min at 95° C., followed by 25 cycles of 95° C. for 30 s, 58° C. for 60 s and 72° C. for 60 s and a final extension at 72° C. for 10 minutes. Only target nucleic acids where the target nucleic binding region of the capture probe hybridized exactly to the target nucleic acid are amplified. Following amplification, amplicons are sequenced and aligned to a reference genome. A number of nucleic acid fragments having one or more mutations is determined, and are compared to a reference value to determine if the subject has cancer.

Example 3. Method of Amplifying Nucleic Acids for Target-Specific Enrichment

In some cases, the concentration of cell-free DNA in a plasma sample may be too low for target-specific enrichment of tumor-derived DNA to be performed; in such cases, amplification of the cell-free DNA may first be used.

In one example, a blood sample is obtained from a human patient and is centrifuged to separate plasma from remaining blood components (e.g., red blood cells, white blood cells and platelets). Cells are removed from plasma by centrifugation for 10 minutes at 1,000-2,000×g using a refrigerated centrifuge. Centrifugation for 15 minutes at 2,000×g depletes platelets in the plasma sample. Following centrifugation, the plasma sample is immediately transferred into a clean polypropylene tube using a Pasteur pipette. The sample is maintained at 2-8° C. while handling. Prior to PCR amplification, terminal unpaired nucleotides are removed from the ends of the cell-free nucleic acid fragments using an exonuclease, capable of hydrolyzing terminal phosphodiester bond, thereby removing any terminal unpaired bases (e.g., an overhang). DNA fragments with 5' overhangs are blunted by filling in a recessed 3' terminus with DNA polymerase in the presence of dNTPs. Double-stranded adapters comprising a BtsCI Type-IIs nuclease recognition sequence and a primer binding site are ligated to each blunt end of the cell-free nucleic acid. Specifically, the BtsCI nuclease recognition sequence is positioned in the adapter such that following ligation of the adapter to the end of the cell-free nucleic acid, a BtsCI Type-IIs nuclease can cleave the adaptor from the cell-free nucleic acid at a junction (e.g., the cleavage site) between the adapter and the cell-free nucleic acid. Following ligation of the adapters to the cell-free nucleic acid, PCR amplification is performed using primers capable of binding the primer binding site on the adapter. PCR amplification is carried out using Go Taq®Green Master Mix. Each PCR reaction mixture consists of 10 μl PCR master mix; 4 μM of each of the forward and reverse primers, and 250 ng DNA extract and the sample volume is brought to 20 μl by deionized water. Thermal cycling is started by a first denaturation step of 4 min at 95° C., followed by 25 cycles of 95° C. for 30 s, 58° C. for 60 s and 72° C. for 60 s and a final extension at 72° C. for 10 minutes. Following amplification, approximately 1 unit of BtsCI nuclease is added to the sample, and the sample transferred to a heat bath at 37° C. for 30 minutes to cleave the adapters from the amplified nucleic acid fragments (e.g., at the junction between the adapter and the nucleic acid fragment). The products (e.g., amplicons) from the amplification are subsequently enriched for tumor-derived DNA and analyzed to detect cancer in the subject, as described in Example 2.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for processing a cell-free nucleic acid molecule from a biological sample, the method comprising:
(a) ligating an adapter to each end of a cell-free nucleic acid molecule, wherein the adapter comprises a recognition sequence for a restriction endonuclease configured to cleave the adapter from the cell-free nucleic acid molecule;
(b) amplifying the cell-free nucleic acid molecule comprising the adapter at each end, thereby generating an amplified cell-free nucleic acid molecule; and (c) separating at least one adapter from the amplified cell-free nucleic acid molecule by digesting the adaptor at the recognition sequence using a corresponding restriction endonuclease.

2. The method of claim 1, wherein the cell-free nucleic acid molecule is double stranded.

3. The method of claim 1, wherein the restriction endonuclease is a Type IIs nuclease.

4. The method of claim 3, wherein the Type IIs nuclease is selected from the group consisting of BtsCI, FOKI, AP endonuclease, and Si endonuclease.

5. The method of claim 1, wherein the concentration of a plurality of the cell-free nucleic acid molecules ranges from 10 to 10000 genomes per milliliter in the biological sample.

6. The method of claim 1, wherein the biological sample is selected from the group consisting of whole blood, blood plasma, blood serum, urine, cerebrospinal fluid, buffy coat, and a combination of any thereof.

7. The method of claim 1, further comprising repairing one or more ends of the cell-free nucleic acid molecule.

8. The method of claim 7, wherein the repairing comprises blunting at least one of the one or more ends of the cell-free nucleic acid molecule to comprise at least one of a terminal 5'-phosphate group or a 3'-hydroxyl group.

9. The method of claim 8, wherein the repairing further comprises attaching a deoxyadenosine nucleotide at the one or more ends of the cell-free nucleic acid molecule.

10. The method of claim 1, wherein the adapter is double stranded.

11. The method of claim 1, further comprising hybridizing at least one probe to each end of the amplified cell-free nucleic acid molecule, wherein
each probe comprises a given sequence that is complementary to at least one end of the amplified cell-free nucleic acid molecule, and wherein each nucleotide of the given sequence of each probe hybridizes with the amplified cell-free nucleic acid molecule.

12. The method of claim 1, further comprising:
(d) subjecting the amplified cell-free nucleic acid molecule to sequencing to obtain a plurality of sequence reads corresponding to the cell-free nucleic acid molecule;
(e) aligning the plurality of sequence reads to a reference genome; and
(f) determining a set of genomic positions in the reference genome at which ends of the plurality of sequence reads occur at a rate above threshold, thereby determining a nucleic acid fragmentation pattern.

13. A method for processing a cell-free nucleic acid molecule from a biological sample, the method comprising:
(a) ligating an adapter to each end of the cell-free nucleic acid molecule from a biological sample, wherein an end of the adapter that is ligated to the cell-free nucleic acid molecule comprises an adenine base or a thymine base;
(b) amplifying the cell-free nucleic acid molecule comprising the adaptor at each end, thereby generating an amplified cell-free nucleic acid molecule comprising an amplified adapter at each end, wherein the amplified adaptor comprises one of a uracil base, a uridine base, or a deoxyuridine base in a position of the thymine base or complementary to the adenine base; and
(c) separating at least one amplified adapter from the amplified cell-free nucleic acid molecule by converting the uracil base, uridine base, or deoxyuridine base to an apurinic/apyrimidinic site (AP site) and then generating a nick at the AP site using a corresponding endonuclease while keeping the amplified cell-free nucleic acid molecule intact.

14. The method of claim 13, wherein conversion of the uracil base, uridine base, or deoxyuridine base to an AP site is with a Uracil-DNA Glycosylase (UDG).

15. The method of claim 13, wherein the amplifying comprises applying one or more primers comprising one of a uracil base, a uridine base, or a deoxyuridine base at a 3' end of the one or more primers.

16. The method of claim 14, wherein the endonuclease is an AP endonuclease.

17. The method of claim 16, further comprising treating the amplified cell-free nucleic acid molecule with an additional nuclease specific for a single-stranded nucleic acid molecule, thereby separating the adapter sequence from the cell-free nucleic acid molecule.

* * * * *